US010352891B2

United States Patent
Davis

(10) Patent No.: US 10,352,891 B2
(45) Date of Patent: Jul. 16, 2019

(54) ELECTRODE AND USE THEREOF

(71) Applicant: Oxford University Innovation Limited, Oxford (GB)

(72) Inventor: Jason Davis, Oxford (GB)

(73) Assignee: Oxford University Innovation Limited, Oxford (GB)

(*) Notice: Subject to any disclaimer, the term of this patent is extended or adjusted under 35 U.S.C. 154(b) by 758 days.

(21) Appl. No.: 14/412,179

(22) PCT Filed: Jul. 2, 2013

(86) PCT No.: PCT/GB2013/051749
§ 371 (c)(1),
(2) Date: Dec. 30, 2014

(87) PCT Pub. No.: WO2014/006394
PCT Pub. Date: Jan. 9, 2014

(65) Prior Publication Data
US 2015/0177180 A1 Jun. 25, 2015

(30) Foreign Application Priority Data

Jul. 3, 2012 (GB) .................................. 1211775.0

(51) Int. Cl.
*G01N 27/327* (2006.01)
*G01N 27/02* (2006.01)
(Continued)

(52) U.S. Cl.
CPC ....... *G01N 27/3275* (2013.01); *G01N 27/026* (2013.01); *G01N 27/3276* (2013.01);
(Continued)

(58) Field of Classification Search
None
See application file for complete search history.

(56) References Cited

U.S. PATENT DOCUMENTS 6,846,654 B1    1/2005  Blackburn et al.
7,435,384 B2 *  10/2008  Fish ................. G01N 33/54313
                                                            422/81

(Continued)

FOREIGN PATENT DOCUMENTS

CN      101957375 A    1/2011
WO      01/61053 A2    8/2001
(Continued)

OTHER PUBLICATIONS

Communication pursuant to Rule 164(2)(b) and Article 94(3) EPC, dated Dec. 16, 2015, for European Application No. 13 733 454.6-1554, 12 pages.

(Continued)

*Primary Examiner* — Tamir Ayad
(74) *Attorney, Agent, or Firm* — Klarquist Sparkman, LLP

(57) ABSTRACT

The application relates to an electrode for use in the electrochemical detection of target species, and in particular for the detection of insulin. The application enables insulin to be detected with high selectivity and with a detection limit in the picomolar range or lower. The electrodes of the invention can easily be reused and are ideally suited for use in point-of-care diagnostics. In a preferred embodiment, the electrode comprises an antibody modified, polyethylene glycol (PEG) monolayer assembled on a gold surface. In a second embodiment, the electrode comprises a chemisorbed zwitterionic carboxybetaine polymer obtained by photopolymerisation of carboxybetaine methacrylate (CBMA). This allows the use of non-Faradaic analysis to determine the insulin concentration even in undiluted blood serum.

18 Claims, 13 Drawing Sheets

(51) Int. Cl.
A61B 5/1468 (2006.01)
G01N 27/07 (2006.01)
A61B 5/145 (2006.01)
A61B 5/1486 (2006.01)

(52) U.S. Cl.
CPC ........... A61B 5/1468 (2013.01); A61B 5/1486 (2013.01); A61B 5/14532 (2013.01); A61B 5/14546 (2013.01); G01N 27/07 (2013.01); G01N 27/327 (2013.01); G01N 27/3271 (2013.01); G01N 2333/62 (2013.01)

(56) References Cited

U.S. PATENT DOCUMENTS

| 9,599,613 B2 * | 3/2017 | Ratner ............. G01N 33/54373 |
| 2003/0087296 A1 | 5/2003 | Fujita et al. |
| 2009/0061533 A1 | 3/2009 | Minami et al. |

FOREIGN PATENT DOCUMENTS

| WO | 2012/009932 A1 | 1/2012 | |
| WO | WO2013013220 | * 1/2013 | ............. G01N 33/80 |

OTHER PUBLICATIONS

Katz et al., "Probing Biomolecular Interactions at Conductive and Semiconductive Surfaces by Impedance Spectroscopy: Routes to Impedimetric Immunosensors, DNA-Sensors, and Enzyme Biosensors," *Electroanalysis* 15(11):913-947, 2003.

Zhang et al., "Dual-Functional Biomimetic Materials: Nonfouling Poly(carboxybetaine) with Active Functional Groups for Protein Immobilization," *Biomacromolecules* 7:3311-3315, 2006.

Bae et al., "Detection of insulin-antibody binding on a solid surface using imaging ellipsometry," *Biosensors and Bioelectronics* 20:895-902, 2004.

Brault et al., "Ultra-low fouling and functionalizable zwitterionic coatings grafted onto $SiO_2$ via a biomimetic adhesive group for sensing and detection in complex media," *Biosensors and Bioelectronics* 25:2276-2282, 2010.

Carr et al., "Uniform zwitterionic polymer hydrogels with a nonfouling and functionalizable crosslinker using photopolymerization," *Biomaterials* 32:6893-6899, 2011.

Gobi et al., "Self-assembled PEG monolayer based SPR immunosensor for label-free detection of insulin," *Biosensors & Bioelectronics* 22:1382-1389, 2007.

Guo et al., "Carbohydrate-Based Label-Free Detection of *Escherichia coli* ORN 178 Using Electrochemical Impedance Spectroscopy," *Anal. Chem.* 84:241-246, 2012.

Hoogvliet et al., "Electrochemical Pretreatment of Polycrystalline Gold Electrodes to Produce a Reproducible Surface Roughness for Self-Assembly: A Study in Phosphate Buffer pH 7.4," *Anal. Chem.* 72:2016-2021, 2000.

International Search Report dated Dec. 12, 2013, for corresponding International Application No. PCT/GB2013/051749, 7 pages.

La Belle et al., "A cytokine immunosensor for multiple sclerosis detection based upon label-free electrochemical impedance spectroscopy," *Biosensors and Bioelectronics* 23:428-431, 2007.

Luo et al., "Ultrasensitive Label Free Electrical Detection of Insulin in Neat Blood Serum," *Anal. Chem.* 85:4129-4134, 2013.

Manickam et al., "A CMOS Electrochemical Impedance Spectroscopy (EIS) Biosensor Array," *IEEE Transactions on Biomedical Circuits and Systems* 4(6):379-390, Dec. 2010.

Pei et al., "Reversible Electrochemical Switching of Polymer Brushes Grafted onto Conducting Polymer Films," *Langmuir* 28:8072-8083, 2012.

Rezaei et al., "Electrochemical impedimetric immunosensor for insulin like growth factor-1 using specific monoclonal antibody-nanogold modified electrode," *Biosensors and Bioelectronics* 26:2130-2134, 2011.

Search Report dated Mar. 7, 2013, for corresponding GB Application No. GB1211775.0, 1 page.

Valsocherová et al., "Ultralow Fouling and Functionalizable Surface Chemistry Based on a Zwitterionic Polymer Enabling Sensitive and Specific Protein Detection in Undiluted Blood Plasma," *Anal. Chem.* 80:7894-7901, 2008.

Vyas et al., "Modifying Randles Circuit for Analysis of Polyoxometalate Layer-by-Layer Films," *J. Phys. Chem. B* 114:15818-15824, 2010.

Xiao et al., "Preparation of electrode-immobilized, redox-modified oligonucleotides for electrochemical DNA and aptamer-based sensing," *Nature Protocols* 2(11):2875-2880, 2007.

Xu et al., "Label-Free Electrochemical Detection for Aptamer-Based Array Electrodes," *Anal. Chem.* 77:5107-5113, 2005.

Xu et al., "The label free picomolar detection of insulin in blood serum," *Biosensors and Bioelectronics* 39:21-25, 2013.

Yoshida et al., "Selection of DNA aptamers against insulin and construction of an aptameric enzyme subunit for insulin sensing," *Biosensors and Bioelectronics* 24:1116-1120, 2009.

Zhang et al., "Development of a spiral piezoelectric immunosensor based on thiol self-assembled monolayers for the detection of insulin," *Journal of Immunological Methods* 338:7-13, 2008.

* cited by examiner

ELECTRODE AND USE THEREOF

The present invention relates to an electrode for use in the electrochemical detection of target species, in particular for the detection of insulin.

BACKGROUND

Insulin is a low molecular weight (ca. 5800 Da) polypeptide hormone produced by the pancreas. It is responsible for regulating the metabolism of carbohydrate and blood glucose levels. The human form is a peptide composed of 51 amino acids, a 21-residue A-chain and a 30-residue B-chain linked by two disulfide bonds. A determination of circulating insulin in serum or plasma is of intrinsic value in the clinical diagnosis and classification of various types of diabetes and related diseases and doping control in athletes.

During the past decade, a variety of detection methods, including those based on radioimmunoassay, mass spectrometry, fluorescence spectrometry and surface plasmon resonance have been developed for the determination of insulin. These methods are, though, either impractical or insensitive and are not translatable to a point-of-care format.

With an increase in the incidence of diabetes, the development of an ultrasensitive, cheap, simple and automated diagnostic test would be of considerable value. In attempting to meet these requirements, electrochemical analyses have received attention. Though amperometric sensors based on the oxidation of insulin have been reported, these operate at high potentials, and accordingly suffer from ascorbic acid and uric acid interference. They are also comparatively insensitive; the blood content of insulin is normally below 80 pM between meals, much lower than the detection limits of most of electrochemical sensors reported to date.

Electrochemical impedance spectroscopy (EIS) is a technique that is capable of sensitively monitoring the changes in capacitance or charge-transfer resistance associated with the specific binding of certain materials to a suitably modified electrode surface. Some immunoassays based on EIS have been demonstrated for the detection of relatively large protein molecules (MW>20 kD). However, EIS has generally not been applied to the analysis of smaller molecules, such as low molecular weight polypeptides, where the impact on impedance resulting from interfacial binding would be expected to be much lower than in the case of large proteins; this is a particularly significant consideration in the context of complex biological fluids containing very low concentrations of the molecules of interest.

SUMMARY OF THE INVENTION

The present inventors have now found an assay system for detecting insulin that is highly selective, extends linearly across the entirely clinically relevant concentration range, and exhibits detection limits in the low picomolar range. The interfaces can easily be reused and so are ideally suited for use in point-of-care diagnostics.

In particular, the present inventors have surprisingly established that physiological samples containing insulin are susceptible to quantitative analysis via electrochemical impedance spectroscopy with exceptional selectivity and sensitivity. The inventors have also found that the sensitivity of these assay systems can be enhanced still further by applying non-Faradaic electrochemical impedance techniques, by analysing the phase change in the electrical signal occurring when the insulin binds to the probe molecules on the electrode surface, and by making use of electrodes prepared using a specific multi-step surface modification protocol based on the photopolymerisation of photopolymerisable betaine monomers. This multi-step surface modification protocol can also be applied to the preparation of electrodes for use in the electrochemical detection of target species other than insulin.

One aspect of the present invention thus relates to an electrode for use in electrochemical impedance spectroscopy, which electrode comprises: (a) a substrate having a planar surface; and (b) probe molecules disposed on said planar surface; wherein said probe molecules are capable of binding selectively to insulin.

In a further aspect, the present invention provides a method for detecting insulin in an electrochemical impedance spectroscopy technique, wherein the method comprises: (a) contacting an electrode of the present invention with a carrier medium comprising insulin; and (b) detecting an electrical signal.

The present invention also provides an electrochemical impedance spectrometer comprising an electrode of the present invention.

In a still further aspect, the present invention provides use of an electrode of the present invention for detecting insulin by an electrochemical impedance spectroscopy technique.

Furthermore, the present invention provides a method of making an electrode for use in an electrochemical impedance spectroscopy technique, which method comprises: (a) attaching photopolymerisable monomers to the planar surface of a substrate, thereby obtaining a modified surface having a layer of polymerisable monomers disposed thereon; then (b) contacting said modified surface with further photopolymerisable monomers, and optionally crosslinking monomers, and photochemically polymerising the monomers, thereby generating an electrode comprising polymers disposed on said planar surface.

In a preferred aspect of the invention, this method further comprises (c) attaching probe molecules capable of specific binding to a target species to said polymers. The target species is preferably insulin.

In a further aspect, the present invention provides an electrode which is obtainable by the above method of making an electrode of the present invention. The invention further provides a method for detecting a target species in an electrochemical impedance spectroscopy technique, wherein the method comprises: (a) contacting the electrode which is obtainable by the above method of making an electrode of the present invention with a carrier medium comprising said target species; and (b) detecting an electrical signal. The invention still further provides an electrochemical impedance spectrometer comprising an electrode which is obtainable by the above method of making an electrode of the present invention, as well as use of an electrode which is obtainable by the above method of making an electrode of the present invention for detecting a target species by an electrochemical impedance spectroscopy technique.

Further preferred features and embodiments are described in the accompanying description and the appended claims.

(A) An ideal typical Nyquist plot of Faradaic EIS and (B) the Randles equivalent circuit used for data fitting.

Figure 2:
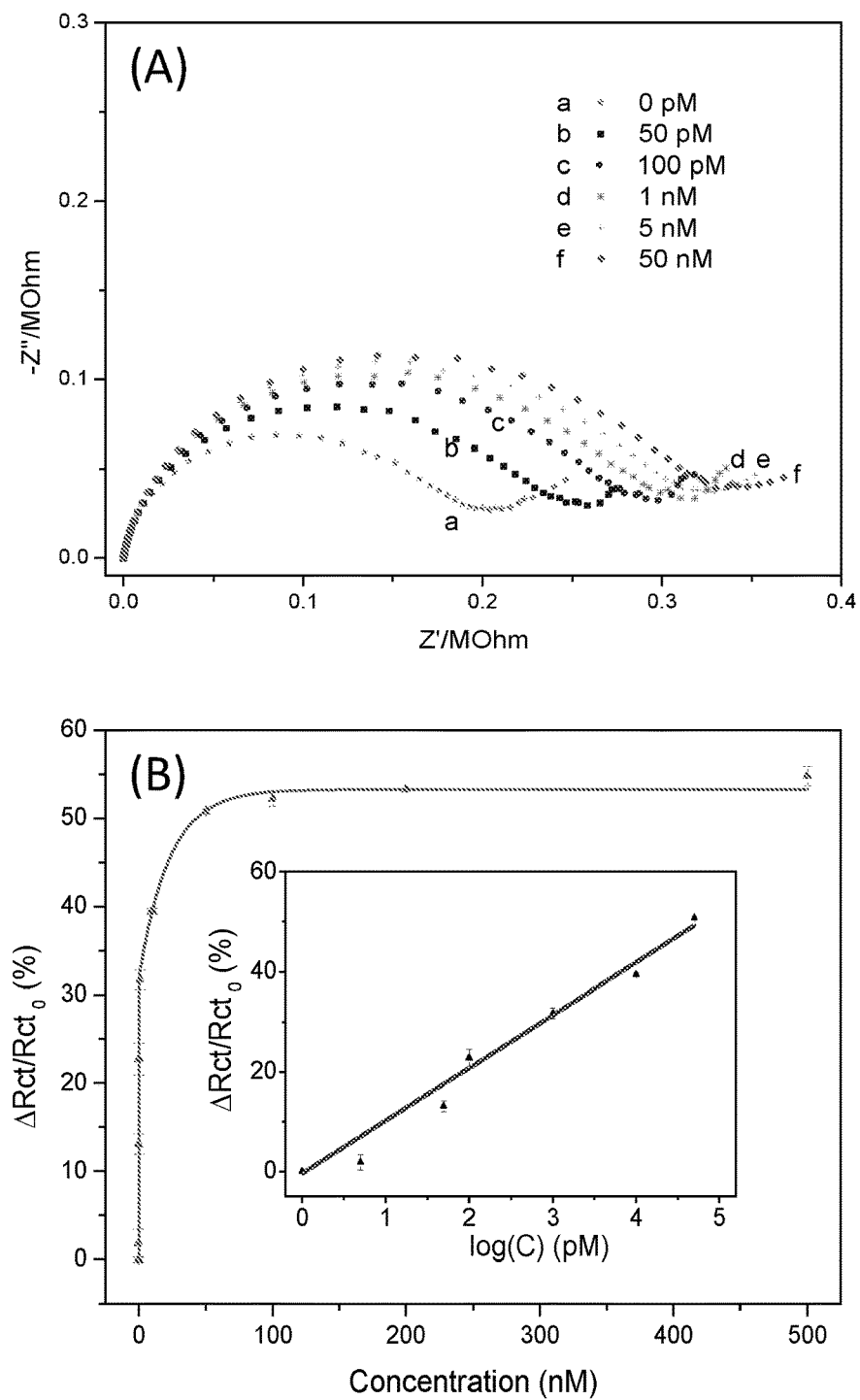

FIG. 2 shows typical Faradaic impedance spectra corresponding to the biosensor of Example 1 after the incubation in PBST solution with different concentrations: (A) curves from inner to outer represent 0 pM, 50 pM, 100 pM, 1 nM, 10 nM, and 50 nM insulin, respectively; (B) normalized charge-transfer resistance ($R_{ct}$) changes of the biosensor after the incubation with different concentrations of insulin protein in PBST (10 mM, pH 7.4) containing 1.0 mM $Fe(CN)_6^{3-/4-}$ and 0.1 M KCl; Inset shows the corresponding calibration curve for the insulin biosensors.

Figure 3:
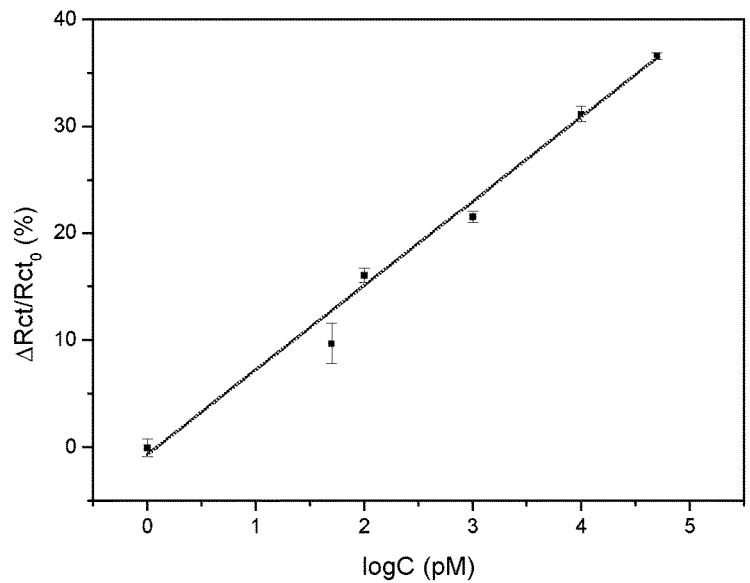

FIG. 3 shows a calibration curve for "in situ" assays of insulin in 10% blood serum as described in Example 1. The biosensor surfaces were incubated in PBST (10 mM, pH 7.4) solution containing 1.0 mM $Fe(CN)_6^{3-/4-}$ 0.1 M KCl and 10% blood serum, spiked with different concentrations of insulin, and EIS measurements subsequently carried out in the same solution.

Figure 4:
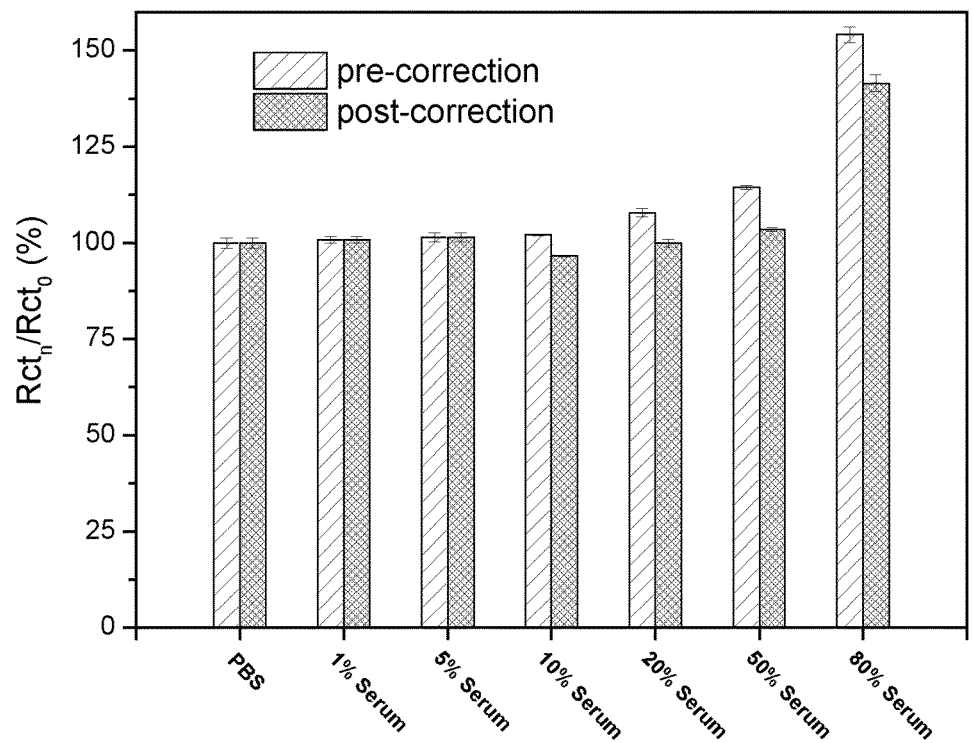

FIG. 4 shows the effect of blood serum concentration as described in Example 1 on the sensor response to insulin before (left column) and after (right column) correction. Electrode surfaces were incubated in PBST (10 mM, pH 7.4) solution containing 100 pM insulin and different volume percents of blood serum for 30 min, and then rinsed with PBST before "ex situ" EIS measurements in PBST containing 1.0 mM $Fe(CN)_6^{3-/4-}$ and 0.1 M KCl. The measured data were then corrected by subtraction of EIS contributions from the insulin in the serum itself as calculated from the calibration curve.

Figure 5:
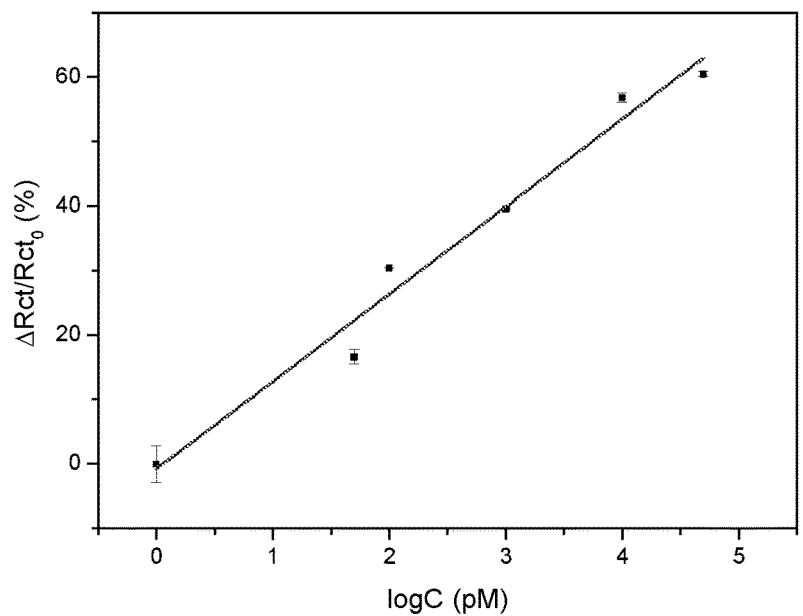

FIG. 5 shows a calibration curve for the "ex situ" assays of insulin in 50% blood serum as described in Example 1. Electrode surfaces were incubated in PBST (10 mM, pH 7.4) solution containing 1.0 mM $Fe(CN)_6^{3-/4-}$, 0.1 M KCl and 50% blood serum, spiked with different concentrations of insulin, and EIS measurements were carried out in PBST (10 mM, pH 7.4) solution containing 1.0 mM $Fe(CN)_6^{3-/4-}$ and 0.1 M KCl after rinsing with PBST.

Figure 6:
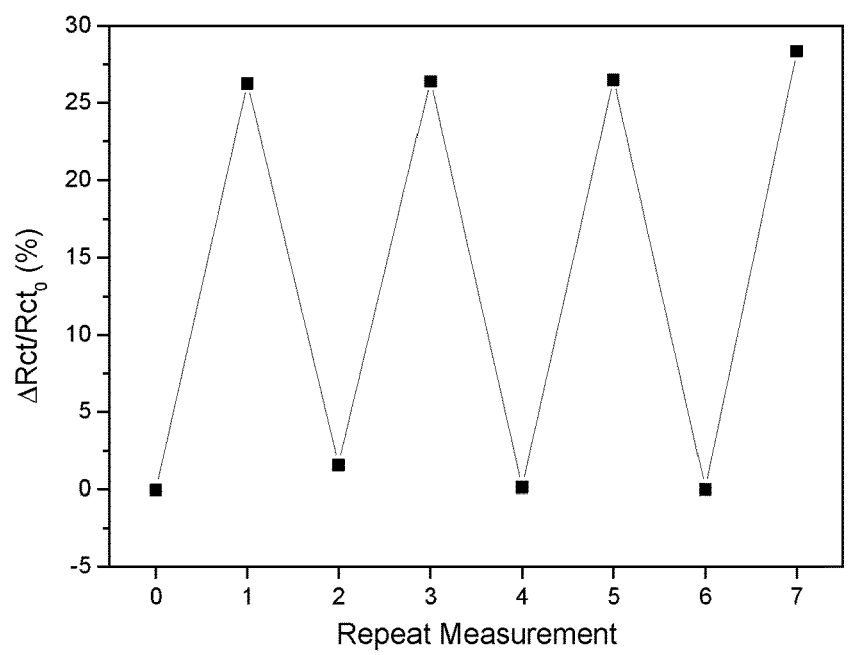

FIG. 6 shows the sensory surface regeneration of the sensor of Example 1 by immersion in 0.2 M Gly-HCl buffer containing 1% DMSO for 5 min prior to rinsing with PBST, and impedance analysis in PBST (10 mM, pH 7.4) solution containing 1.0 mM $Fe(CN)_6^{3-/4-}$ and 0.1 M KCl.

Figure 7:
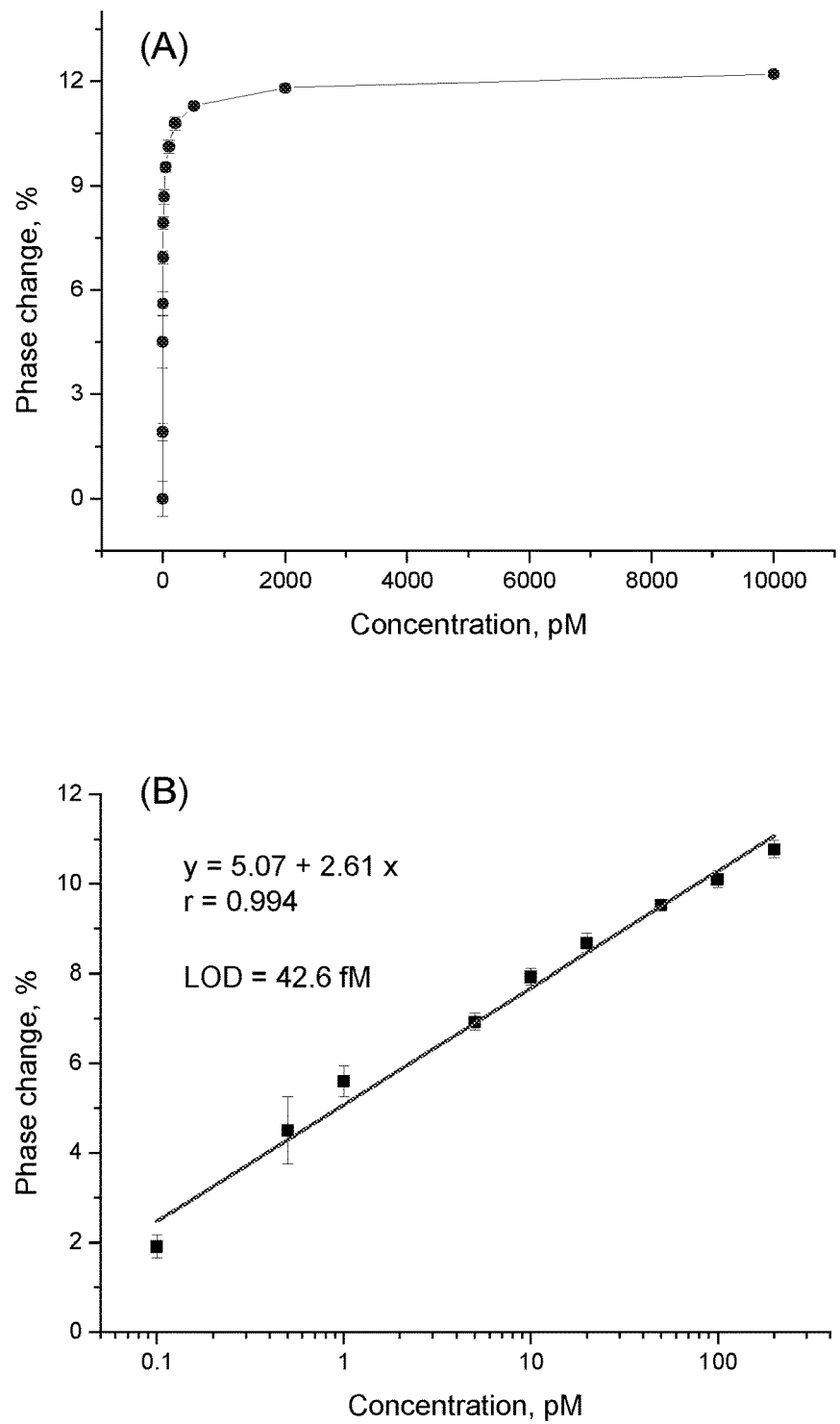

FIG. 7 shows the results of phase change non-Faradaic EIS analysis of insulin samples measured at a series of concentrations on a sensor as described in Example 2: (A) response data; (B) calibration curve.

Figure 8:
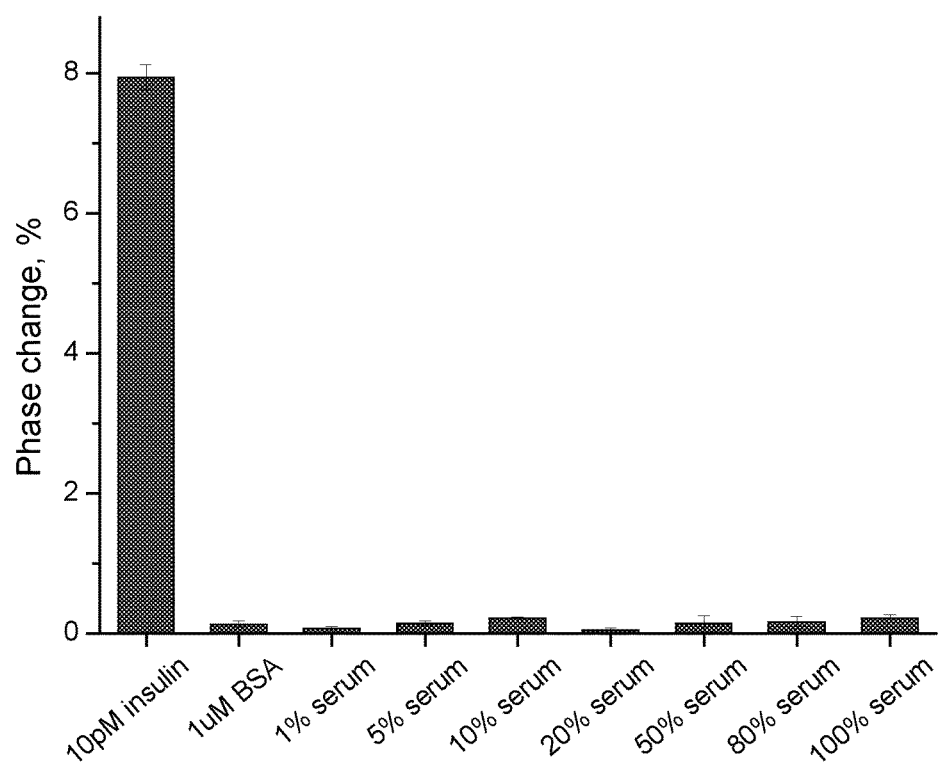

FIG. 8 shows a phase change non-Faradaic EIS analysis of a representative insulin sample and a series of control samples on a sensor as described in Example 2.

Figure 9:
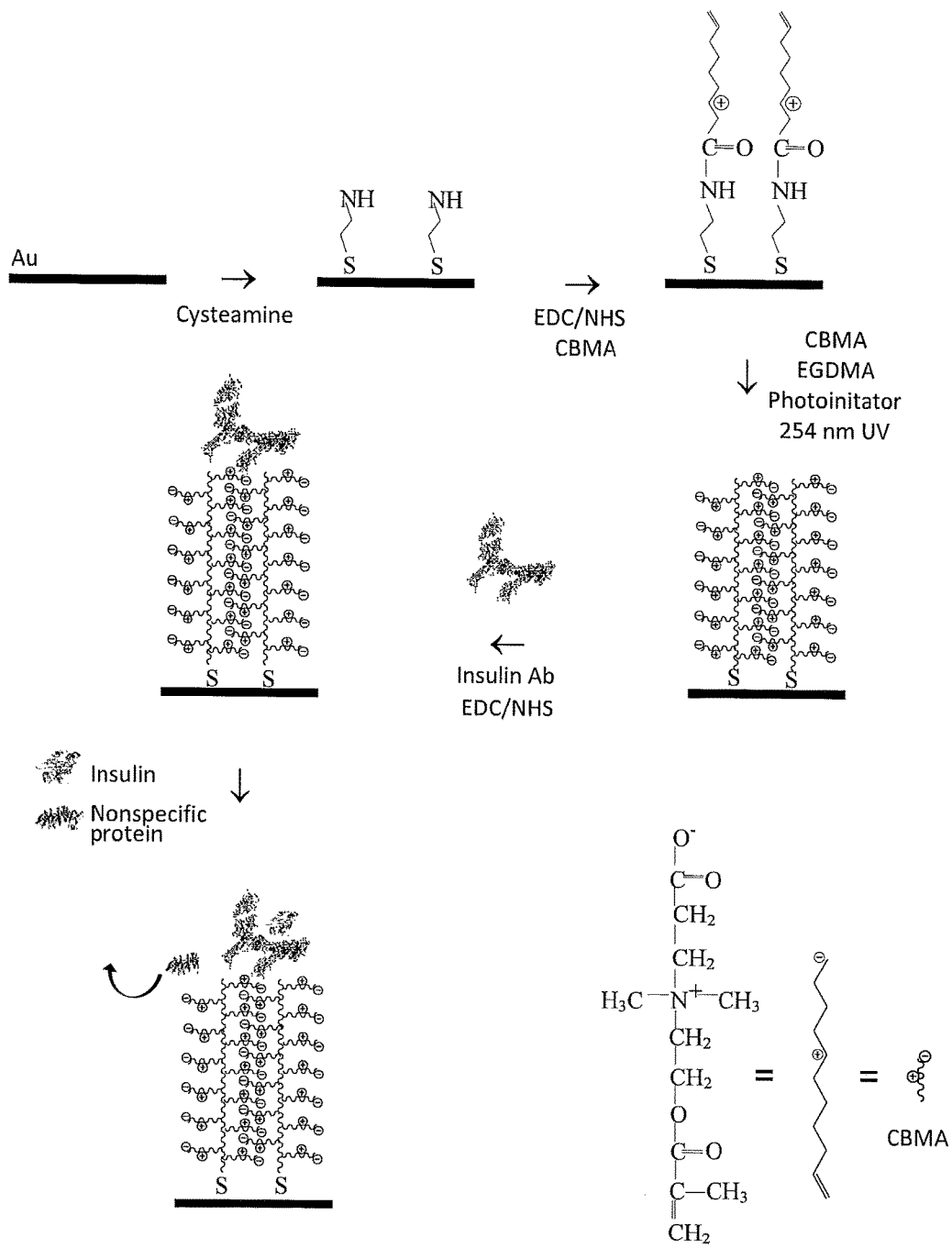

FIG. 9 shows a schematic illustration of one method for preparing an electrode by functionalising a substrate surface with an insulin antibody according to one embodiment of the present invention.

Figure 10:
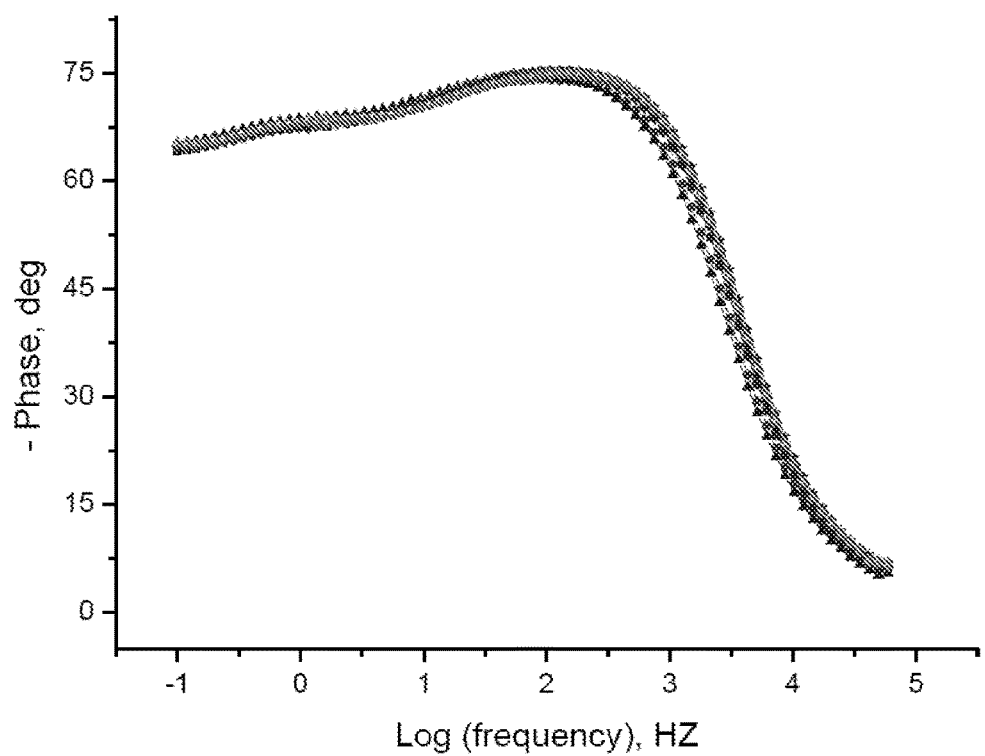

FIG. 10 shows non-Faradaic EIS Bode phase plots of an electrode modified with PCBMA recorded at different time intervals (specifically, at days 1, 4, 6, 8, 11, 13, 15, 19, 22, 25, 28 and 32) in PBS (10 mM, pH 7.4), as described in Example 3.

Figure 11:
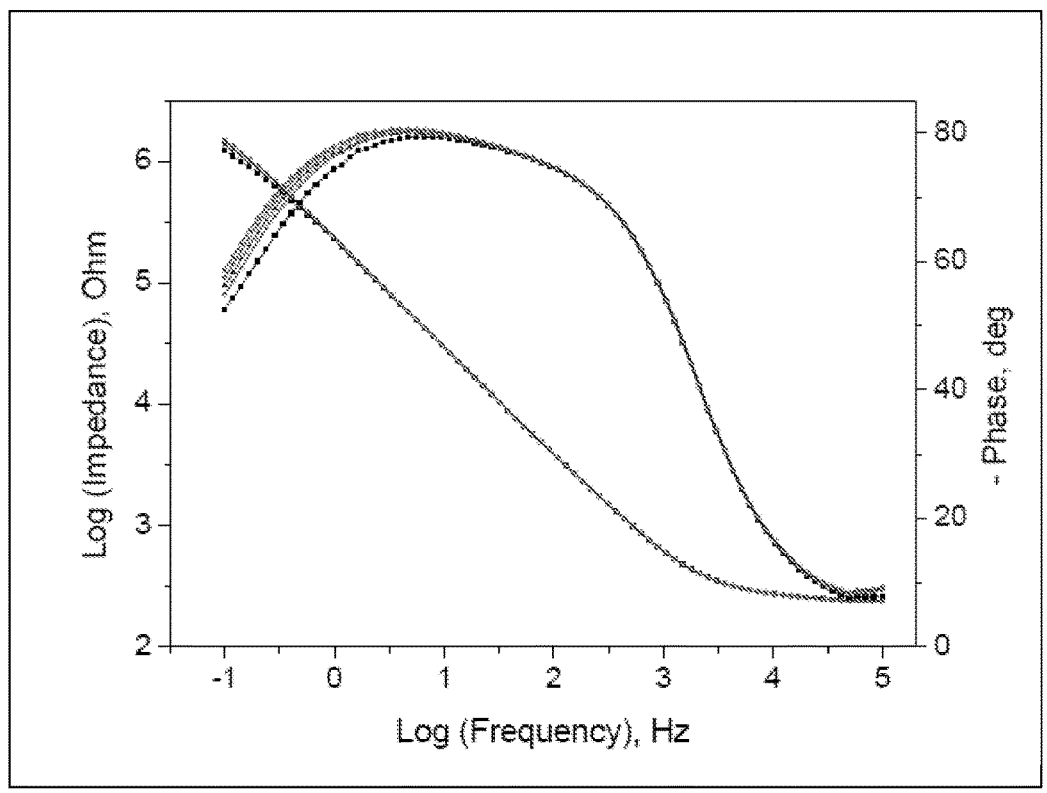

FIG. 11 shows non-Faradaic EIS Bode plots of the biosensor interfaces as described in Example 3 after exposure to calibrated concentrations of insulin. Measurements were made in 10 mM PBS (pH 7.4) across a frequency range of 0.1-100K Hz. The closely matched curved peaking at a value of approximately 6 and generally decreasing as log(frequency) increases are measurements of log(impedance). The curves that first increase as log(frequency) increases, then peak and subsequently decrease as log(frequency) continues to increase, are measurements of phase change. The latter curves can be distinguished by the insulin sample concentration particularly at low values of log(frequency) below approximately 0; in this region the lowest curve corresponds to 0 pM insulin, with successively higher curves corresponding to 1 pM, 10 pM, 100 pM and, finally, 2000 pM insulin.

Figure 12:
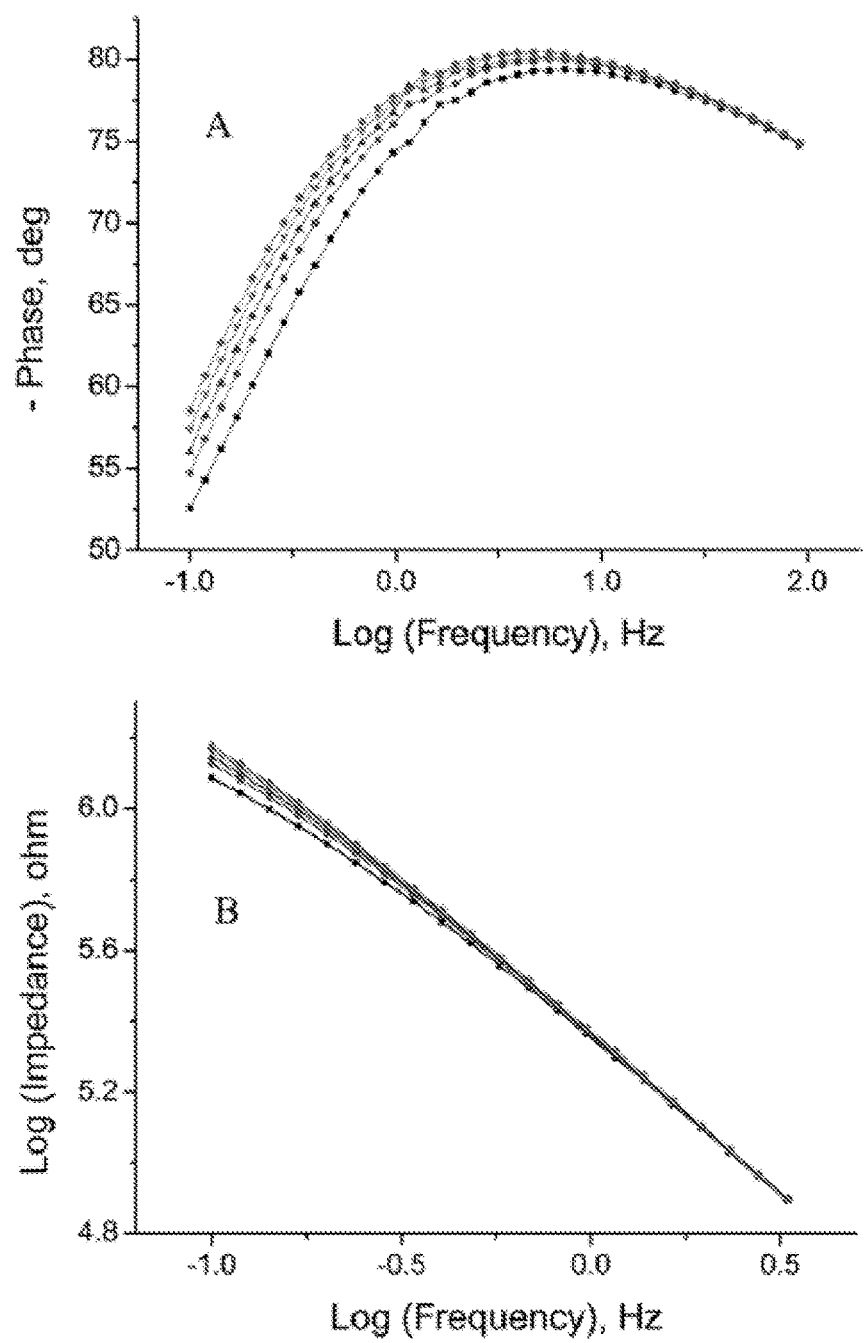

FIG. 12 shows (A) phase curves, depicting the detected phase offset between input and output signals as a function of applied frequency and (B) impedance curves of non-Faradaic EIS Bode plots of a typical sensory surface as described in Example 3. For both graphs (A) and (B), to the extent that discrete curves can be identified, the lowest curve corresponds to 0 pM insulin, with successively higher curves corresponding to 1 pM, 10 pM, 100 pM and, finally, 2000 pM insulin.

Figure 13:
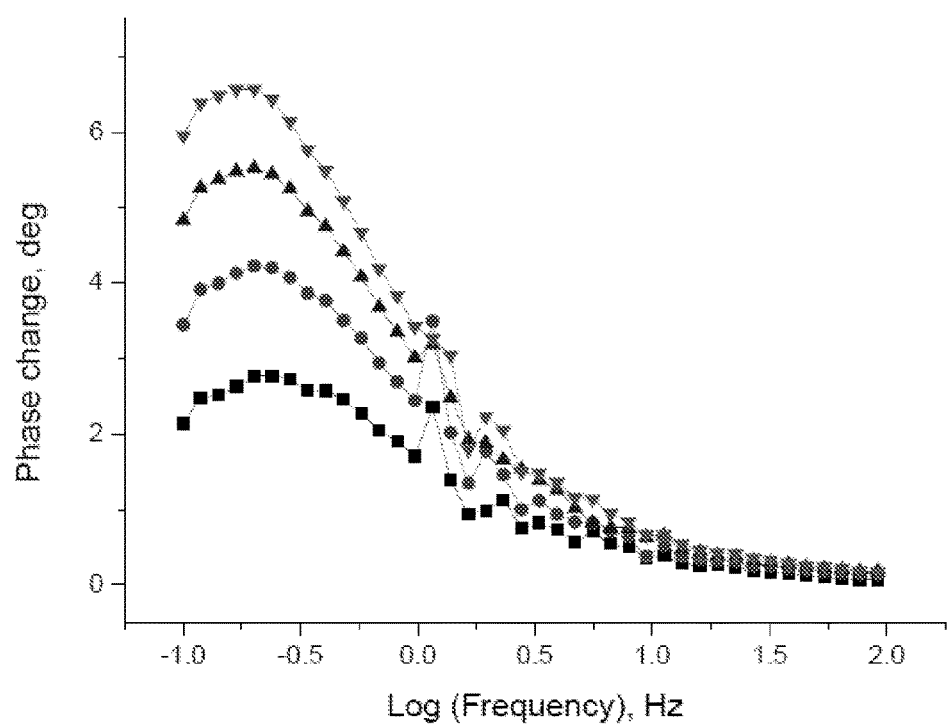

FIG. 13 shows the neat phase changes of biosensors in the low frequency domain, as described in Example 3. The lowest curve corresponds to 1 pM insulin, with successively higher curves corresponding to 10 pM, 100 pM and, finally, 2000 pM insulin.

Figure 14:
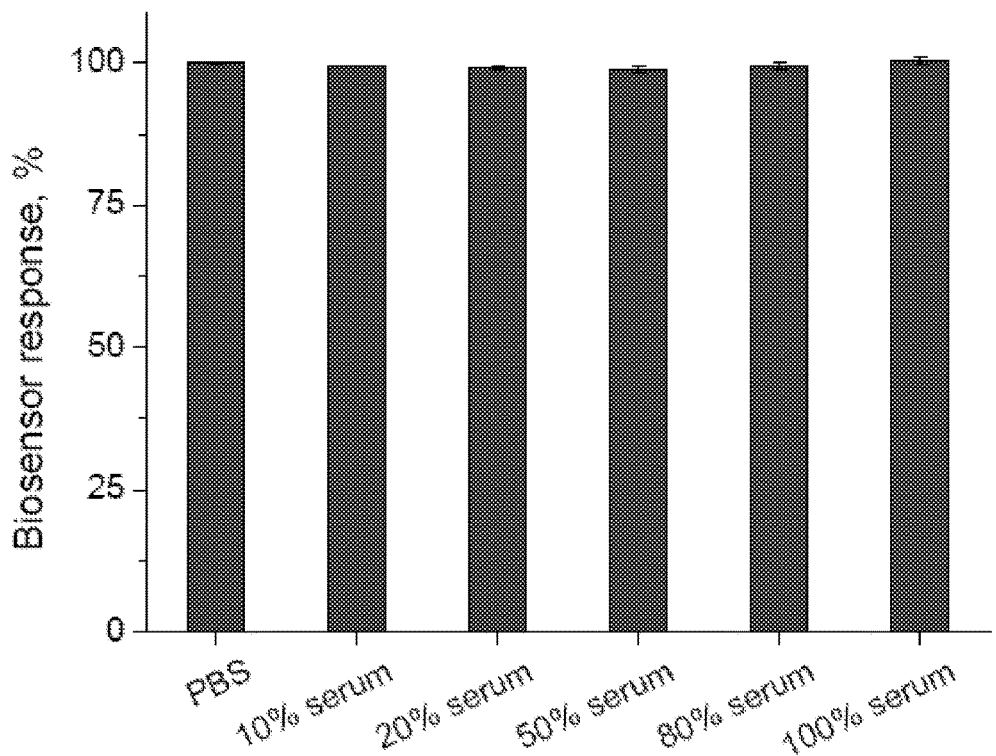

FIG. 14 shows biosensor response to 50 pM insulin in progressively increasing serum concentration with the response in pure PBS taken as 100%, as described in Example 3. The response is based on the EIS phase change before and after insulin spiking, and the assay errors are within 2%. Error bars represent the standard deviations of three measurement repeats.

Figure 15:
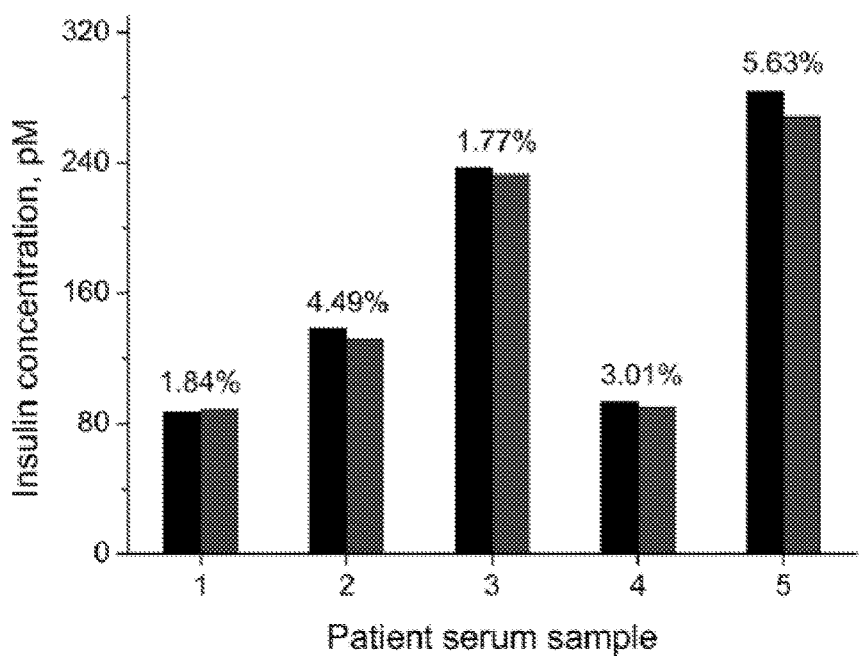

FIG. 15 shows representative comparative real patient serum sample assays with the non-Faradaic EIS method as described in Example 3 (macro disc electrodes; each sample analyzed in triplicate) and a clinically approved chemiluminescent immunoassay. The % differences are shown. Note that for the groups of adjacent blocks, the left-hand block corresponds to chemiluminescence results and the right-hand block to EIS results.

Figure 16:
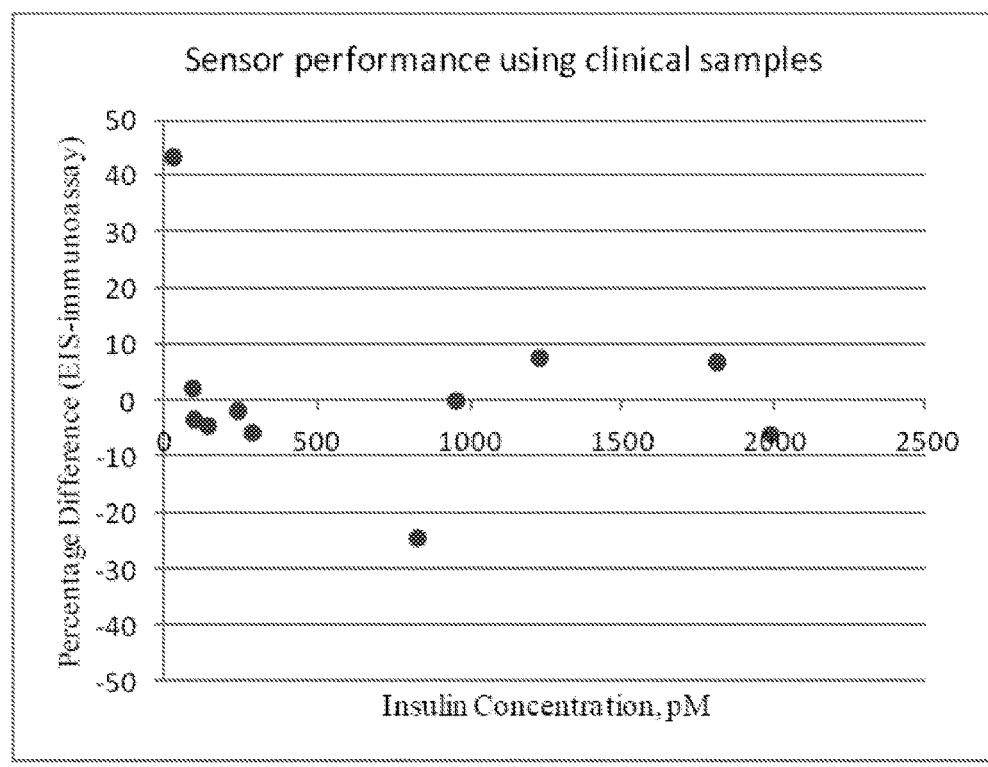

FIG. 16 shows a Bland Altman plot of biosensor performance, as compared to a clinical standard chemiluminescence assay and as further described in Example 3. The data shown here was acquired at both macro disk gold electrodes and screen printed microelectrode arrays.

DETAILED DESCRIPTION

Optional and preferred features of the present invention are now described. Any of the features described herein may be combined with any of the other features described herein, unless otherwise stated.

The electrodes of the present invention comprise probe molecules disposed on the planar surface of a substrate. The probe molecules are capable of binding selectively to a target species. In electrodes for use in the EIS detection of insulin, the target species is insulin. In certain electrodes of the present invention, the target species may be a species other than insulin, as described further herein.

The substrate of the electrode may comprise any electrically conducting material. The substrate may comprise a metal or carbon. The metal may be a metal in elemental form or an alloy of a metal. Optionally, the whole of the substrate comprises a metal or carbon. The substrate may comprise a transition metal. The substrate may comprise a transition metal selected from any of groups 9 to 11 of the Periodic Table. The substrate may comprise a metal selected from, but not limited to, rhenium, iridium, palladium, platinum, copper, indium, rubidium, silver and gold. The substrate may comprise a metal selected from gold, silver and platinum. The substrate may comprise a carbon-containing material, which may be selected from edge plane pyrolytic graphite, basal plane pyrolytic graphite, glassy carbon, boron doped diamond, highly ordered pyrolytic graphite, carbon powder and carbon nanotubes.

In a preferred embodiment, the substrate comprises gold, for example the substrate is a gold substrate.

The surface of the substrate is planar, which includes a generally flat surface, typically without indentations, protrusions and pores. Such substrate surfaces can be readily prepared, before probe molecules and any associated linker molecules are bound to the surface, by techniques such as polishing with fine particles, e.g. spraying with fine particles, optionally in a sequence of steps where the size of the fine particles is decreased in each polishing step. The fine particles may, for example, comprise a carbon-based material, such as diamond, and/or may have particles with diameters of 10 µm or less, optionally 5 µm or less, optionally 3 µm or less, optionally 1 µm or less, optionally 0.5 µm or less, optionally 0.1 µm or less. Following polishing, the substrate surface may be washed, e.g. ultrasonically, optionally in a suitable liquid medium, such as water, e.g. for a period of at least 1 minute, e.g. from about 1 minute to 10 minutes. Optionally, the substrate surface may be washed with an abrasive, e.g. acidic, solution, for example following the polishing and, if used, ultrasonic washing steps. The abrasive solution may comprise an inorganic acid, e.g. $H_2SO_4$, and/or a peroxide, e.g. $H_2O_2$, in a suitable liquid medium, e.g. water. Optionally, the substrates can be electrochemically polished, which may follow any steps involving one or more of polishing with fine particles, washing e.g. ultrasonically and/or using an abrasive solution. The electrochemical polishing may involve cycling between an upper and lower potential until a stable reduction peak is reached, e.g. an upper potential of 0.5 V or more, optionally 1 V or more, optionally 1.25 V or more, and a lower potential of 0.5 V or less, optionally 0.25 V or less, optionally 0.1 V or less.

The probe molecule preferably comprises or is a binding species selected from an antibody, an antibody fragment, an aptamer, an oligosaccharide, a peptide, and a protein. Preferably, the probe molecules comprise or are a binding species selected from one or more of an antibody, a nucleic acid and a peptide. Most preferably the probe molecules comprises or are an antibody.

If the probe molecules comprise an antibody or an antibody fragment, the antibody or the antibody fragment may be selected from one or more of the classes IgA, IgD, IgE, IgG and IgM. In a preferred embodiment, the antibody or antibody fragment is of the IgG type. The antibody binds selectively to the target species. The antibody or antibody fragment may be derived from a mammal, including, but not limited to, a mammal selected from a human, a mouse, a rat, a rabbit, a goat, a sheep, and a horse. In an embodiment, the probe molecules comprise an antibody of the IgG type derived from a mouse.

If the probe molecules comprise an aptamer, the aptamer may be selected from a peptide aptamer, a DNA aptamer and a RNA aptamer.

As indicated above, preferably, the probe molecules comprise a binding species selected from one or more of an antibody, a nucleic acid and a peptide. The binding species may be directly attached to the surface of the substrate or attached to the surface of the substrate via a linker species. If a linker species is present on the surface of the substrate, the linker species may for example comprise a self-assembling monolayer or may comprise a self-assembling monolayer-anchored polymer.

The electrode as described herein may be formed by forming a self-assembling monolayer of linker species, optionally activating the linker species, and then binding the binding species to at least some of the linker species. The electrode as described herein may also be formed by forming a self-assembling monolayer, forming a polymer linker species on the self-assembling monolayer (i.e, to obtain a self-assembling monolayer-anchored polymer), optionally activating the polymer linker species, and then binding the binding species to at least some of the linker species.

Preferably, the substrate surface having the probe molecules thereon, as a whole, is selective for the target species (e.g., for insulin). If the substrate surface having the probe molecules thereon is selective for the target species, this indicates that substantially only or only the target species will bind to the surface (via binding to the probe molecules), and other species (e.g., present in the carrier medium with the target species) will not bind, or not bind to any significant degree, to other parts of the substrate surface or other species thereon. Such selective substrate surfaces may be termed highly selective substrate surfaces (or highly selective electrode surfaces).

In an embodiment, the probe molecule is of the formula A-L-B, wherein A is a moiety bound to the planar surface of the substrate, L is a linker moiety and B is a moiety capable of binding selectively to insulin.

'A' may be selected from any appropriate binding group, depending on the nature of the material of the substrate. For example, A may be selected from, but is not limited to, biotin, hydrazine, alkynyl, alkylazide, amino, hydroxyl, carboxy, thio, aldehyde, phosphinothioester, maleimidyl, succinyl, succinimidyl, isocyanate, ester, strepavidin, avidin, neuavidin, and biotin binding proteins. If the substrate comprises a noble material, e.g. gold, silver or platinum, A is preferably thiol (or thiolate), which may be selected from —SH and —S—. If the substrate comprises a metal that has a layer of oxide on its surface, e.g. copper, A may be a carboxy group.

L may be any species that covalently links A to B. L is preferably a species that allows formation of a self-assembling monolayer. For example, L may be a hydrocarbon moiety. L may comprise an alkylene moiety comprising at least 2 carbons, the alkylene moiety being directly attached to A; optionally the alkylene moiety is a straight-chain alkylene moiety. L may comprise an alkylene moiety comprising at least 10 carbons, optionally from 10 to 30 carbons, optionally from 10 to 20 carbons, optionally from 11 to 15 carbon atoms, and the alkylene moiety is optionally a straight-chain alkylene moiety, and the alkylene moiety is directly attached to A.

For the avoidance of doubt, "alkylene" as used throughout this specification means an alkyl group having at least two (for example two) hydrogen atoms removed therefrom, e.g. it means for example alkanediyl. The terms "alkylene" and "alkyl" may be used interchangeably because it is clear from context how many hydrogen atoms of the corresponding (parent) alkane must be removed in order for the group to be attached to other specified functional groups. For example, the group L must be capable of attaching at least to A and to B, thereby meaning that at least two (e.g., two) carbon atoms have been removed from the corresponding alkane.

In an embodiment, L is of the formula —$(CH_2)_n$—(—O—$CH_2$—$CH_2$—)$_m$-D-, wherein n is from 1 to 30 and m is from 0 to 10 and D is a bond or a group bound to B. D may for example be selected from a bond or —(C=O)—, —$OCH_2$—(C=O)—, —(C=O)—NH—, —(C=O)—O—, —$OCH_2$—(C=O)—NH—, —$OCH_2$—(C=O)—OH—, —O— or —NH—. n may for example be from 10 to 20. m may for example be 1 to 5, optionally 2 to 4, optionally 3. Optionally, if D is any one of the species (C=O)—NH—, —(C=O)—O—, —OCH$_2$—(C=O)—NH—, —OCH$_2$—(C=O)—O—, —O— and —NH—, then —NH— or —O— in these species may be derived from a probe molecule, e.g. an antibody, prior to being bound to the linker species L.

B may be selected from a binding species as described above, for example selected from an antibody, an antibody fragment, an aptamer, an oligosaccharide, a peptide, a protein. Such species that bind selectively to target species, i.e. insulin, are available commercially.

In an embodiment, A-L- is a species of formula thiol-$(CH_2)_n$—$(-O-CH_2-CH_2-)_m$-D- wherein n is from 1 to 30 and m is from 0 to 10 and D is a group that binds to B; optionally n, m and D may be as defined above, and thiol is selected from —S— and HS—.

In an embodiment, an electrode as described herein, e.g. having probe molecules thereon, may be produced by providing the substrate having the planar surface, then forming a self-assembling monolayer of linker species on the planar surface, and attaching probe moieties, e.g. antibodies, to at least some of the linker species. The linker species may optionally be activated, e.g. by reaction with an activator, such as N-hydroxysuccinimde (NHS), to allow for facile attachment of the probe moieties to the linker species. In an embodiment, the linker species forming the self-assembling monolayer are of the formula A-L, wherein A is a moiety that binds to the surface of the substrate and L is a linker moiety capable of binding to a moiety (which may be denoted B) which binds to the target species, e.g. an antibody.

In an embodiment, the probe molecules may comprise a polymer that is attached both to: (a) the planar surface of the substrate; and (b) to a moiety B capable of binding selectively to insulin. Preferably said polymer comprises a plurality of pendant betaine groups. A betaine group is a group that comprises both a positively charged cationic functional group that bears no hydrogen atom (e.g., a quaternary ammonium or phosphonium functional group) and a negatively charged functional group (for example a carboxylate group or a sulfonate group). Pendant means that the said betaine groups are side groups extending away from the main chain of the polymer (i.e., the chain derived from repeating monomeric units).

The pendant betaine groups may, for example, each comprise a quaternary ammonium cation and a carboxylate group. For example, the pendant betaine groups may have the formula (I)

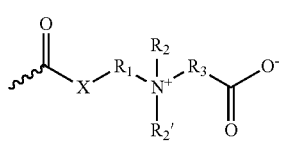

(I)

wherein:
$R_1$ and $R_3$ are the same or different and are each a $C_1$ to $C_5$ alkylene group;
$R_2$ and $R_{2'}$ are the same or different and are each a $C_1$ to $C_5$ alkyl group; and
X is O or NH.

In one exemplary aspect the pendant betaine groups may have the formula (I) wherein $R_1$ and $R_3$ are ethylene, $R_2$ and $R_{2'}$ are methyl and X is O. A polymer containing such pendant groups can be obtained by photopolymerisation of carboxybetaine (alkyl)acrylates such as carboxybetaine methylacrylate (CBMA) and carboxybetaine ethylacrylate (CBEA). In another exemplary aspect the pendant betaine groups may have the formula (I) wherein $R_1$ is propylene, $R_3$ is ethylene, $R_2$ and $R_{2'}$ are methyl and X is NH. A polymer containing such pendant groups can be obtained by photopolymerisation of carboxybetaine (alkyl)acrylamides such as carboxybetaine acrylamide.

The polymer may for example have a hydrocarbon main chain, for example a main chain that is a straight chain or branched chain alkylene moiety (e.g., having at least 10 carbon atoms, optionally at least 50 carbon atoms, optionally at least 100 carbon atoms). Typically where the polymer comprises a plurality of pendant betaine groups the polymer comprises at least 5, or at least 10, for example at least 25 pendant betaine groups. Such polymers are for example obtainable by photopolymerisation of photopolymerisable monomers containing a photopolymerisable carbon-carbon double bond (as well as a betaine group, should the polymer comprise a plurality of pendant betaine groups). For example, monomers comprising (alkyl)acrylate groups such as acrylate, methacrylate and ethyacrylate can be used.

In one preferred aspect of the present invention, the electrodes are obtainable by carrying out the method of making an electrode of the present invention, as described in more detail herein.

The present application also relates to a method for detecting insulin in an electrochemical impedance spectroscopy technique, wherein the method comprises: (a) contacting an electrode of the present invention with a carrier medium comprising insulin; and (b) detecting an electrical signal at the working electrode.

Electrochemical impedance spectroscopy (EIS) is known to the skilled person. Generally, a varying ac potential is applied on a bias (or DC) potential between a working electrode and a counter electrode. Generally, EIS involves scanning across a range of ac frequencies. The ratio of the input signal (typically the varying potential) to the output signal (typically the varying current) allows the impedance to be calculated. There is generally a phase difference between the input signal and the output signal, such that the impedance can be considered as a complex function, having a real part (sometimes termed Z') and an imaginary part (sometimes termed Z").

Figure 1:
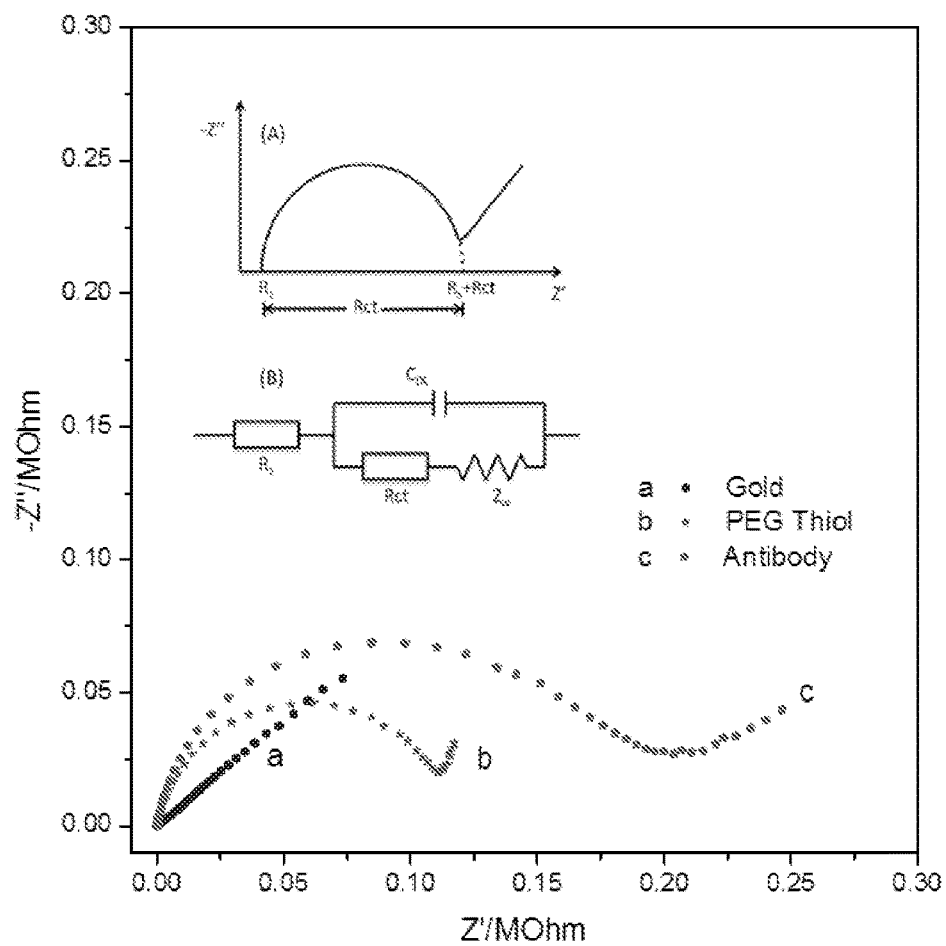
FIG. 1 shows Nyquist plots of different electrodes recorded in PBST (10 mM, pH 7.4) solution containing 1.0 mM $Fe(CN)_6^{3-/4-}$ and 0.1 M KCl as described in Example 1: (a) bare gold electrode; (b) PEG SAM interfaces; (c) subsequently prepared antibody modified interfaces; Inset.

The real and imaginary parts of impedance can be plotted against one another, e.g. in the form of a Nyquist plot, as illustrated in FIG. 1. By fitting the impedance data to an assumed equivalent circuit, the electron transfer resistance can be determined, which is one means through which the binding event can be assessed. Alternatively, the method may comprise measuring the phase difference itself.

The frequency range of the varying ac potential applied may be from 0.05 Hz to 10 kHz. The amplitude of the applied ac potential, which is typically in the form of a sine wave, may be from 1 mV to 100 mV, optionally from 5 mV to 50 mV, optionally from 5 mV to 20 mV, optionally from 5 mV to 15 mV, optionally 8 mV to 12 mV, optionally about 10 mV. The bias potential (or direct current potential) may be set at any desired potential. If a redox probe is present in the carrier medium, the bias potential may be set at the electrode potential of the redox probe under the conditions at which the method is carried out.

In one aspect, a redox probe may be present in the carrier medium, and the method may involve Faradaic EIS. If a redox probe is present, it may be a transition metal species, wherein the transition metal can adopt two valence states (e.g. a metal ion (M) being able to adopt M(II) and M(III) states). In an embodiment, the redox probe contains a metal ion, wherein the metal of the metal ion is selected from iron, ruthenium, iridium, osmium, cobalt, tungsten and molybdenum. In an embodiment, the redox probe is selected from $Fe(CN)_6^{3-/4-}$, $Fe(NH_3)_6^{3+/2+}$, $Fe(phen)_3^{3+/2+}$, $Fe(bipy)_2^{3+/2+}$, $Fe(bipy)_3^{3+/2+}$, $Ru^{3+/2+}$, $RuO_4^{3-/2-}$, $Ru(CN)_6^{3-/4-}$, $Ru(NH_3)_6^{3+/2+}$, $Ru(en)_3^{3+/2+}$, $Ru(NH_3)_5(Py)^{3+/2+}$, $Ir^{4+/3+}$, $Ir(Cl)_6^{2-/3-}$, $Ir(Br)_6^{2-/3-}$, $Os(bipy)_2^{3+/2+}$, $Os(bipy)_3^{3+/2+}$, $OxCl_6^{2-/3-}$, $Co(NH_3)_6^{3+/2+}$, $W(CN)_6^{3-/4-}$, $Mo(CN)_6^{3-/4-}$, optionally substituted ferrocene, polyferrocene, quiniones, such as p-benzoquinone and hydroquinone and phenol In an embodiment, the redox probe is an iron-containing species in which iron is in Fe(II) and/or Fe(III) states. In an embodiment, the redox probe is $Fe(CN)_6^{3-/4-}$. The redox probe may be present in the carrier medium an amount of from 0.1 mM to 100 mM, optionally from 0.5 mM to 10 mM, optionally from 0.5 mM to 2 mM, optionally from 0.5 mM to 1.5 mM, optionally about 1 mM.

In a particularly preferred aspect of the invention, however, the EIS technique is a non-Faradaic EIS technique. In this aspect, no redox probe is added to the carrier medium. For example, the carrier medium may contain no externally added, i.e., exogenous, redox probe, for example it may comprise no redox probe. The present inventors have found that non-Faradaic EIS provides more sensitive results for the detection of insulin than Faradaic EIS. This was an unexpected result because EIS assays are conventionally dominated by Faradaic methods in which a redox probe is added to the carrier medium (because the resistive effects of a binding event at a surface are greatly amplified by sampling the impact of this on the current generated by a redox probe in large excess).

The carrier medium is preferably in liquid form. The carrier liquid may be any liquid in which the target species (e.g. insulin) can be suspended or dissolved. In an embodiment, the carrier liquid comprises water. In an embodiment, the carrier liquid comprises a biological fluid. A biological fluid may be a fluid that has been obtained from a subject, which may be a human or an animal. In an embodiment, the carrier liquid comprises an undiluted biological fluid. An undiluted biological fluid in the present context is a biological fluid obtained from a subject, e.g. a human or animal, that has not been diluted with another liquid, although additives such as a redox probe, may be present in the undiluted biological fluid. The biological fluid may be selected from blood, urine, tears, saliva, sweat, and cerebrospinal fluid.

Optionally, the carrier medium comprises a biological fluid obtained from a subject, e.g. a human or animal, and a diluent. The diluent may be added to the biological fluid after it has been obtained from the subject. The diluent may include a liquid medium, e.g. a liquid medium selected from water and an alcohol, e.g. an alcohol, e.g. ethanol. The carrier medium may further comprise a buffer. The buffer may comprise a phosphate.

The method may comprise calculating the concentration of the target species (e.g., insulin) from the electrical signal. The electrical signal may be converted into impedance data and then converted to the concentration of the target species (e.g., insulin) from the electrical signal. The electrical signal may be converted into charge transfer resistance data, or phase change data, and then converted to the concentration of the target species (e.g., insulin) from the electrical signal. The method may involve comparing the data obtained in the electrochemical impedance spectroscopy technique, e.g. from the electrical signal, the impedance data, the charge transfer resistance data, or the phase change data, and comparing the data with data obtained in a calibration step, to obtain the concentration of the target species (e.g., insulin). The method may involve an initial calibration step that determines a relationship between the concentration of the target species (e.g., insulin) and electrochemical data obtained from the electrochemical signal in the electrochemical impedance spectroscopy technique; the electrochemical data may be selected from impedance data, charge transfer resistance data and phase change data; the relationship may be used to convert the electrochemical data obtained from a sample of interest in the electrochemical impedance spectroscopy technique to the concentration of the target species (e.g., insulin) in the sample.

The inventors have found that calculating the concentration of insulin from a phase change in an electrical signal occurring upon binding of the insulin to the probe molecules gives rise to a particularly sensitive insulin assay compared to other methods known in the art for quantifying electrochemical impedance spectroscopy data. Accordingly, it is a particularly preferred aspect of the method of the invention that the concentration of insulin is calculated from a phase change in an electrical signal occurring upon binding of the insulin to the probe molecules. Suitable phase data may for example be provided directly by potentiostat software (e.g., using commercially available Autolab potentiostats). Phase data may be sampled at any frequency and in the presence of any concentration of target species.

The concentration of the target species (e.g., insulin) in the carrier medium may be 0.1 pM or more, optionally 0.2 pM or more, optionally 0.5 pM or more, optionally 1.0 pM or more. The concentration of the target species (e.g., insulin) in the carrier medium may be 100 nM or less, optionally 80 nM or less, optionally 50 nM or less, optionally 10 nM or less. The concentration of the target species (e.g., insulin) in the carrier medium may be from 0.1 pM to 100 nM, optionally from 0.2 pM to 100 nM, optionally from 0.5 pM to 50 nM.

The present inventors have found that it is possible to regenerate the electrode that has been bound to target species (e.g., insulin), by dissociating bound target species (e.g., insulin) from the electrode. The method may therefore involve, after contacting the electrode with the carrier medium such that target species (e.g., insulin) is bound to the probe molecules, dissociating target species (e.g., insulin) from the probe molecules. The dissociating may comprise contacting of the electrode surface having target species (e.g. insulin) thereon with an acidic liquid medium, optionally having a pH of 6 or lower, optionally a pH of 5 or lower, for example a pH of 4 or lower. The acidic liquid medium may contain an acidic substance, for example an acidic buffer (for example, glycine hydrochloride). The acidic liquid medium may be aqueous or non-aqueous. For example, it may be a non-aqueous medium comprising a non-aqueous solvent such as DMSO.

The method may further comprise, after dissociating insulin from the probe molecules, reusing the electrode in one or more further methods for detecting insulin in an electrochemical impedance spectroscopy technique. Each such further method may comprise carrying out a method for detecting insulin of the present invention.

The present invention also relates to an electrochemical impedance spectrometer, wherein the spectrometer comprises an electrode as defined herein. The electrochemical impedance spectrometer may be of a standard design. The electrochemical impedance spectrometer may comprise an electrode of the present invention as a working electrode, a counter electrode, and, if desired a reference electrode. The electrochemical impedance spectrometer preferably comprises a means for applying, controlling and varying a potential between the working and counter electrodes, and a means for measuring the resultant current. The electrochemical impedance spectrometer preferably comprises a potentiostat for controlling the potential and measuring the resultant current. The electrochemical impedance spectrometer preferably comprises a means for calculating impedance data from the potential applied and the resultant current. The electrochemical impedance spectrometer may comprise a means for calculating electron transfer resistance of the working electrode.

The electrochemical impedance spectrometer is preferably for detecting insulin present in a carrier medium at a concentration of 0.1 pM or more, optionally 0.2 pM or more, optionally 0.5 pM or more, optionally 1.0 pM or more.

The present invention also relates to the use of an electrode as described herein, or an electrochemical impedance spectrometer as described herein, for the detection of a target species, e.g. insulin. The use may include detecting the presence of and/or detecting the concentration of the target species, e.g. insulin. The use may be for detecting insulin present in a carrier medium at a concentration of 0.1 pM or more, optionally 0.2 pM or more, optionally 0.5 pM or more, optionally 1.0 pM or more.

The present inventors have found that a particularly non-fouling and stable electrode surface, ideally suited for use in the technically demanding circumstances associated with insulin detection by EIS, can be obtained by effecting substrate surface functionalisation via a multi-step procedure making use of photopolymerisation techniques. In particular, the present inventors have devised a method of making an electrode for use in an electrochemical impedance spectroscopy technique, which method comprises:

(a) attaching photopolymerisable monomers to the planar surface of a substrate, thereby obtaining a modified surface having a layer of polymerisable monomers disposed thereon; then
(b) contacting said modified surface with further photopolymerisable monomers, and optionally crosslinking monomers, and photochemically polymerising the monomers, thereby generating an electrode comprising polymers disposed on said planar surface.

Advantageously, this method leads to a polymer-modified substrate surface which is substantially non-fouling. Furthermore, the method steps can be carried out in aqueous solution and by photoinitiation under moderate and safe laboratory conditions. That may be contrasted with an alternative method in which a polymer is generated in solution and subsequently drop-cast or spin-coated onto a surface, which leads to relatively uncontrolled reactions and potentially unstable surfaces (due to the absence of covalent attachment of polymer to substrate surface). The present method is also advantageous over an alternative method in which an initiator self-assembled monolayer is generated and then a free radical reaction is initiated under inert atmosphere and solvent and with the monomer added (which is inconvenient, relatively uncontrolled and potentially hazardous).

For ease of understanding, FIG. 9 shows a schematic illustration of this methodology for preparing an electrode. It is emphasised that this Figure shows only a specific embodiment of the present invention and is not representative of the full scope of the present method.

The photopolymerisable monomers may be attached to the planar surface of a substrate in step (a) by methods known in the art, for example using the methods described herein for attaching a linker moiety 'L' to a substrate surface. It will be appreciated that depending on the chemical nature of both the substrate and the monomers, it may be possible to attach the monomers to the surface directly. Alternatively, the surface may first be chemically activated to introduce chemically reactive functional groups (such as, but not limited to, thiol or amine groups), which enable attachment of the monomers. For example, cysteamine is commonly used to introduce reactive amine functional groups onto gold substrates; the thiol group on the cysteamine reagent binds to the substrate and the resulting free amine groups can readily be reacted with a suitable functional groups, such as a carboxylic acid group, on the monomers (in the case of a carboxylic acid group on the monomers, resulting in formation of an amide bond). Typically the step of attaching the photopolymerisable monomers comprises covalently or semi-covalently attaching photopolymerisable monomers to the planar surface of the substrate (i.e., formation of a covalent or semi-covalent bond between the photopolymerisable monomers and the substrate surface). For the avoidance of doubt, attaching photopolymerisable monomers to the planar surface of a gold substrate via a gold-sulfur bond is included within the scope of the term "covalently or semi-covalently attaching" (the gold-sulfur bond being regarded as a covalent or semi-covalent bond, e.g. a semi-covalent bond).

The modified surface having a layer of photopolymerisable monomers disposed thereon may be a self-assembled monolayer.

In the method of the invention, step (a) is carried out before step (b). Thus, step (a) is carried out, then step (b) is carried out. This means that (typically covalent) attachment of a layer of photopolymerisable monomers is substantially complete before the modified surface is contacted with further photopolymerisable monomers, optionally crosslinking monomers, and the photochemical polymerisation is carried out. This multi-step nature of the method leads to the generation of a stable and homogenously modified substrate surface.

Typically, but not essentially, the photopolymerisable monomers used in steps (a) and (b) are the same.

Preferably the photopolymerisable monomers (and further photopolymerisable monomers) are photopolymerisable betaine monomers. However, other photopolymerisable monomers may be used. For example other photopolymerisable monomers capable of forming hydrogel polymers or other zwitterionic photopolymerisable monomers may be used.

The photopolymerisable betaine monomers comprise a photopolymerisable functional group and a betaine group. As explained in the foregoing disclosure, a betaine group is a group that comprises both a positively charged cationic functional group which bears no hydrogen atom (e.g., a quaternary ammonium or phosphonium functional group) and a negatively charged functional group (for example a carboxylate group or a sulfonate group).

The photopolymerisable group may be any group susceptible to photopolymerisation under conditions suitable for electrode surface modification. In an embodiment, the photopolymerisable monomers may each comprise a photopolymerisable carbon-carbon double bond. For example, the photopolymerisable monomers may comprise (alkyl)acrylate groups, such as acrylate, methacrylate and/or ethyacrylate groups. In the case of a photopolymerisable betaine monomer, the photopolymerisable group is a group other than the positively charged cationic functional group of the betaine group and the negatively charged functional group of the betaine group.

In an embodiment, the polymerisable betaine monomers each comprise a quaternary ammonium cation and a carboxylate group. The photopolymerisable betaine monomers may, for example, be of the formula (II)

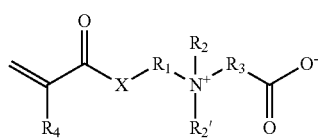

(II)

wherein:
$R_1$ and $R_3$ are the same or different and are each a $C_1$ to $C_5$ alkylene group;
$R_2$ and $R_{2'}$ are the same or different and are each a $C_1$ to $C_5$ alkyl group;
$R_4$ is a hydrogen atom or a $C_1$ to $C_5$ alkyl group; and
X is O or NH.

In exemplary aspects of the method, the photopolymerisable betaine monomers are selected from carboxybetaine methacrylate (CBMA), carboxybetaine acrylamine (CBAA) and carboxybetaine ethylacrylate (CBEA).

Crosslinking monomers may optionally be used in the step (b). One suitable crosslinker is ethyleneglycol dimethacrylate (EGDMA), although other crosslinkers known in the art can also be used.

A photoinitiator is typically used to initiate the photochemical polymerisation of the monomers in the step (b). Any suitable photoinitator can be used of the many photoinitiators known in the art. Non-limiting examples of suitable photoinitiators include methylbenzoyl formate and 1-hydroxycyclohexyphenyl ketone.

The photopolymerisation may result in polymers that comprise a plurality of pendant betaine groups, as described elsewhere herein. The polymers may for example comprise at least 5, or at least 10, for example at least 25 pendant betaine groups.

The photopolymerisation may result in a polymer that may for example have a hydrocarbon main chain, for example a main chain that is a straight chain or branched chain alkylene moiety (e.g., having at least 10 carbon atoms, optionally at least 50 carbon atoms, optionally at least 100 carbon atoms).

In a preferred aspect, this method further comprises (c) attaching probe molecules capable of specific binding to a target species to said polymers. The probe molecules may be attached directly to the polymers provided both the probe molecules and polymers have suitable accessible reactive functional groups. Alternatively, the polymers, or the probe molecules, may be chemically activated by reacting them with suitable activating compounds known in the art. For example, accessible negatively charged functional groups such as carboxylate groups on pendant betaine groups of the polymer may readily be activated using compounds such as NHS, thereby rendering them chemically reactive to probe molecules such as antibodies.

In an exemplary aspect, the target species is insulin and so the step (c) involves attaching probe molecules capable of specific binding to insulin (e.g., insulin antibodies) to said polymers.

However, as noted in the foregoing disclosure this method of making an electrode can also be applied to the production of electrodes for use in electrochemical impedance spectroscopy detection of probe molecules that are capable of specific binding to target species other than insulin (herein referred to as "other target species").

Such other target species include proteins, polypeptides, antibodies, nanoparticles, drugs, toxins, harmful gases, hazardous chemicals, explosives, viral particles, cells, multicellular organisms, cytokines and chemokines, ganietocyte, organelles, lipids, nucleic acid sequences, oligosaccharides, chemical intermediates of metabolic pathways and macromolecules. In preferred embodiments, the other target species comprises, consists essentially of, or consists of, a biological molecule, more suitably a biological macromolecule, most suitably a polypeptide.

If the other target species is or comprise a protein, the protein may be selected from, but is not limited to, native proteins, denatured proteins, protein fragments, and prokaryotically or eukaryotically expressed proteins. Protein may have its normal meaning in the art, and most preferably 'protein' refers to a polypeptide molecule. Such polypeptide may comprise modifications such as glycosylation; phosphorylation or other such modifications.

If the other target species is an antibody, the antibody may be selected from one or more of the classes IgA, IgD, IgE, IgG and IgM.

If the other target species is a nanoparticle, the nanoparticle can be selected from, but is not limited to, one or more of insulating, metallic or semiconducting nanoparticles.

If the other target species is a drug, the drug may be selected from, but is not limited to, alcohol (e.g. ethanol), amphetamines, amyl nitrate, heroin, ketamine, anabolic steroids, LSD, solvents, cannabis, cocaine (such as cocaine hydrochloride or 'coke'), tobacco, tranquilisers, crack (i.e. cocaine free base), ecstasy and/or gammhydroxybutyrate (GHB). Alternatively, in some embodiments, the drug may be a medicinal substance.

The other target species may be a candidate drug, e.g. a chemical or biological entity that may be tested or screened for a particular activity or property using the present invention.

If the other target species is a toxin, the toxin may be selected from, but is not limited to, one or more toxins originating from animals, plants, or bacteria.

If the other target species is a viral particle, the viral particle may be selected from, but is not limited to, one or more viral particles with and without a genome.

If the other target species is a cell, the cell may be selected from, but is not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and mycoplasma.

If the other target species is an organelle, the organelle may be selected from, but is not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

If the other target species is a lipid, the lipid may be selected from, but is not limited to, one or more of signalling lipids, structural lipids, phospholipids, glycolipids and fatty acids.

If the other target species is nucleic acid sequence, the nucleic acid sequence may be selected from, but is not limited to, one or more of DNA, cDNA, RNA, rRNA, mRNA, miRNA and tRNA.

If the other target species is an oligosaccharide, the oligosaccharide may be selected from, but is not limited to, one or more of oligosaccharides of human, animal, plant, fungal or bacterial origin.

The other target species may be any antigen or analyte that is indicative of a particular disease. The target may be selected from, for example, C-reactive protein, angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C—C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein; glucose; insulin; TRIG; GPT; HSPA1 B; IGFBP2; LEP; ADIPOQ; CCL2; ENG; HP; IL2RA; SCp; SHBG; and TIMP2.

The other target species may be a target associated with monitoring diabetes. In an embodiment, the target may be selected from glucose, insulin, Interleukin 2 receptor alpha (IL2-RA), C-reactive protein (CRP) and glycated hemoglobin (HbAlc). If the other target is glucose, the probe moieties may be selected from, for example, the molecular recognition element of GDH-FAD assay or a glucose/galactose binding protein ("GGBP") (Scholle, et al., Mol. Gen. Genet 208:247-253 (1987)). If the other target is IL-2RA, the probe moieties may comprise or consist of a monoclonal antibody specific for IL-2RA. If the other target species is or comprises C-reactive protein, preferably this is human C-reactive protein.

It is believed that the multi-step reaction of the present invention gives rise to surfaces having enhanced stability and anti-fouling characteristics with respect to previous polymer-modified electrode surfaces. Accordingly, the present invention is also directed to an electrode which is obtainable by this method of making an electrode. It will be appreciated that such anti-fouling and stability characteristics are particularly advantageous in the context of detection of insulin from physiological samples, where selectivity and sensitivity are both major issues.

The polymer-modified electrodes of the present invention are susceptible to analysis using surface analysis techniques known in the art. For example, electroanalytical methods (such as "reductive stripping") and surface spectroscopic methods (such as X-ray photoelectron spectroscopy and ellipsometry) can be used to confirm that a polymer film is chemically bound to an electrode through sulphur based chemistry. Ellipsometry and atomic force microscopy can be used to define the film thickness and homogeneity. Mass spectroscopy can be used to define the composition of the film. Additional electroanalysis, such as impedance, can be additionally used to define the film stability and thickness.

The electrode obtainable by the method of making an electrode of the present invention can be utilised in a method for detecting a target species in an EIS technique. This method for detecting a target species comprises: (a) contacting the electrode with a carrier medium comprising the target species; and (b) detecting the electrical signal. In an exemplary embodiment, the method is for detecting insulin and thus the carrier medium comprises insulin. However, the method can also be applied for detection of the "other target species" described herein.

Similarly, the invention provides an electrochemical impedance spectrometer comprising an electrode obtainable by the method of making an electrode of the present invention. Preferably this electrochemical impedance spectrometer comprises an electrode that is obtainable by the method of making an electrode of the present invention, wherein the method comprises each the steps (a), (b) and (c) described herein (i.e., which results in an electrode that comprises probe molecules attached to the polymers which are themselves disposed on the planar surface of the electrode substrate). Again, the electrochemical impedance spectrometer is preferably suitable for detecting insulin (i.e., it comprises an electrode which comprises probe molecules capable of binding selectively to insulin). However, also provided are electrochemical impedance spectrometers suitable for detecting "other target species" described herein and which thus comprise an electrode which comprises probe molecules capable of binding selectively to a target species of interest.

Also similarly, the invention provides use of electrode obtainable by the method of making an electrode of the present invention for detecting a target species by an EIS technique. Again, this use preferably comprises use for detecting insulin. However, the use may also be use for detecting "other target species" defined herein.

A particularly preferred aspect of the invention relates to a method for detecting insulin in an electrochemical impedance spectroscopy technique which has at least two, and preferably all, of the following characteristics:

the technique is a non-Faradaic electrochemical impedance spectroscopy technique;

the method comprises calculating the concentration of insulin from the electrical signal, wherein the concentration of insulin is calculated from a phase change in an electrical signal occurring upon binding of the insulin to the probe molecules; and the electrode is obtainable by the method of making an electrode of the present invention (preferably a method which uses photopolymerisable betaine monomers as the photopolymerisable monomers and further photopolymerisable monomers).

The inventors have found that such a method gives rise to an exceptionally selective method for detecting insulin down to very low detection limits (of the orders of 1 pM or lower) in complex biological samples and which is readily applicable to point-of-care diagnostics.

Methods and electrodes provided herein are described below with reference to particular Examples. The invention is not intended to be limited to these particular Examples.

EXAMPLE 1

Insulin Detection by Faradaic EIS, Via Charge-transfer Resistance Analysis, on a PEG-modified Electrode Chemicals and Reagents Human insulin, human blood serum, strepavidin and bovine serum albumin (BSA) were purchased from Sigma Aldrich. Monoclonal anti-insulin antibody (mouse IgG1 isotype) was purchased from Santa Cruz Biotechnology, Inc. 1-ethyl-3-(3-dimethylaminopropyl) carbodiimide (EDC), N-hydroxysuccinimde (NETS) and dimethyl sulphoxide (DMSO) were purchased from Sigma Aldrich. Polyethylene glycol (PEG) containing thiol HS—$C_{11}$-$(EG)_3$-$OCH_2$—COOH was purchased from Prochimia Surfaces, Poland. Phosphate buffered saline (PBS) with Tween-20 (PBST, 10 mM, pH 7.4) was prepared by dissolving PBS tablets (Sigma Aldrich) in ultrapure water with 0.2% v/v Tween-20 added, and filtered using a 0.22 μm membrane filter. All other chemicals were of analytical grade. Ultrapure water (18.2 MΩ/cm) was obtained from a Milli-Q system and used throughout.

Apparatus

Electrochemical experiments were performed on an Autolab Potentiostat 12 equipped with an FRA2 module (Metrohm Autolab B.V.). A conventional three-electrode system with gold disk working electrodes (1.6 mm diameter, BASi), a platinum wire counter, and a silver/silver chloride (Ag/AgCl, filled with 1.0 M KCl) reference electrode (CH Instruments) was used. All potentials reported are relative to the Ag/AgCl reference electrode.

Sensor Surface Preparation

Gold electrodes were first polished sequentially with 3.0, 1.0 and 0.1 μm diamond spray (Kemet International Ltd) then ultrasonically washed in water (ca. 5 min) prior to immersion in hot piranha solution (concentrated $H_2SO_4$: 30% $H_2O_2$, v/v 3:1. Caution: please treat with extreme care!) for 15 min. Finally, the electrodes were electrochemically pre-treated according to a previous report (Xiao Y, Lai R Y, Plaxco K W; 2007 Nature protocols 2: 2875-2880, the content of which is herein incorporated by reference in its entirety) with some alteration. Briefly, cyclic voltammetry (CV) scans were conducted in 0.5 M KOH over the potential range from −0.35 V to −1.35 V at a scan rate of 2 V/s, until curves were stable. Following this treatment, scans were carried out in 0.5 M $H_2SO_4$ over the potential range from −0.35 to 1.5 V (4 V/s) until a stable sharp reduction peak is obtained. The effective surface area of the gold electrode can be calculated during this procedure (Hoogvliet J C, Dijksma M, Kamp B, van Bennekom W P; 2000 Anal Chem 72: 2016-2021, the content of which is herein incorporated by reference in its entirety).

The pre-treated gold electrodes were dried in a flow of nitrogen gas and immediately immersed in a solution of 50 μM HS—$C_{11}$-$(EG)_3$-$OCH_2$—COOH in ethanol for 12 hours at room temperature. After monolayer formation electrodes were rinsed with ethanol, then water and dried in a flow of nitrogen gas, prior to incubation in a solution containing 0.4 M EDC and 0.1 M NHS to activate the terminal carboxyl groups (~40 minutes). Insulin antibodies were subsequently immobilized by dipping the gold electrode in a 1.0 μM antibody solution (PBST, pH 7.4) for 10 hours at 4° C. In order to block the active sites on the electrode surface, the modified electrode was finally soaked in 100 μM BSA for 6 hours at 4° C., then rinsed with PBST prior to analysis.

Electrochemical Impedance Spectroscopy

EIS measurements were conducted with an Autolab Potentiostat 12 equipped with an FRA2 module using a three-electrode system and a frequency range of 0.01 Hz to 10 kHz. The amplitude of the applied sine wave was 10 mV with the direct current potential set at 0.22 V (which is the $E_0$ of the used redox probe). All analyses were carried out in 10 mM PBST solution containing 1.0 mM $Fe(CN)_6^{3-/4-}$ and 0.1 M KCl, and plotted in the form of complex plane diagrams (Nyquist plots) subsequently fitted using a standard Randles equivalent circuit.

Sensor Operation

For the detection of insulin, the prepared receptive interfaces were incubated in 10 mM pH 7.4 PBST with 1.0 mM $Fe(CN)_6^{3-/4-}$ and 0.1 M KCl containing specific concentrations of insulin at room temperature for 30 min, and EIS responses were recorded in the same solution. To evaluate sensor selectivity, strepavidin was initially used. For "in situ" assays in serum (10% v/v with 10 mM PBST, 1.0 mM $Fe(CN)_6^{3-/4-}$, 0.1 M KCl), electrodes were incubated in different concentrations of insulin spiked PBST for 30 min prior to EIS analysis in the same solution. "Ex situ" assays were also run in spiked serum (1-80% v/v with 10 mM PBST, 1.0 mM $Fe(CN)_6^{3-/4-}$, 0.1 M KCl) by electrode incubation for 30 min prior to PBST rinsing and EIS analysis in 10 mM pH 7.4 PBST with 1.0 mM $Fe(CN)_6^{3-/4-}$ and 0.1 M KCl. Used electrode interfaces were regenerated by soaking in 0.2M Gly-HCl buffer at pH 2.0 containing 1% DMSO for 5 min to disassociate the attached insulin, prior to PBST rinsing and re-use.

Results—Biosensor Fabrication

Nyquist impedance plots include a semicircle portion at high frequencies and a linear portion at lower frequencies corresponding to the charge-transfer limited and diffusion processes, respectively. The former can be quantified, through the semicircle diameter, as the charge-transfer resistance ($R_{ct}$) of the modified electrode, when fitted using the standard Randles equivalent circuit (inset in FIG. 1) (as explained, for example in (a) Guo X F, Kulkarni A, Doepke A, Halsall H B, Iyer S, Heineman W R; 2012. Anal Chem 84: 241-246 and (b) Vyas R N, Li K Y, Wang B; 2010 J Phys Chem B 114: 15818-15824; the content of these documents is herein incorporated by reference in their entireties).

Faradaic EIS analyses were initially used to characterise the construction of the receptive surfaces, noting, predictably, sharp increases in $R_{ct}$ on PEG SAM formation (<50Ω to ~120 kΩ) and antibody immobilisation (~200 kΩ, FIG. 1).

Results—Detection of Insulin in Buffer

Despite the comparatively low molecular weight of the target protein, the prepared interfaces were observed to be sensitively responsive to insulin in PBST even in the low picomolar range (FIG. 2). It may be that this sensitivity is, at least partially, aided by the insulin negative charge (the isoelectric point of human insulin is about 5.4) at this pH and the resulting electrostatic repulsion of the redox probe. More detailed analyses reveal a good linear correlation ($R^2$=0.994) between $R_{ct}$ and the logarithmic value of insulin concentration, a linear range of 5 pM to 50 nM, and a detection limit of 1.24±0.01 pM (FIG. 2). The interfacial disassociation constant $K_D$, was calculated to be 0.11±0.01 nM, a value in very good agreement with previous laser-induced fluorescence determination. The prepared interfaces exhibit negligible response (<5% change in baseline signal) to streptavidin or BSA concentrations of up to 100 nM.

Results—Detection of Insulin in Blood Serum

Insulin serum assays were evaluated in two ways. In the first instance, "in situ" assays were carried out with spiked 10% serum in PBST (FIG. 3). Under such conditions reliable linear assessments were possible across the clinically relevant range with a detection limit of 4.70±0.64 pM. By extrapolation of data acquired through such analyses, the levels of insulin present in native (non spiked) serum could be determined at 60.1±3.9 pM, within the reported normal range.

Subsequent "ex situ" analyses were carried out with insulin spiked blood serum at controllable dilution in PBST (FIG. 4). Biosensors were incubated in these solutions and then measured after rinsing with PBST. The assays were effective and remained robust at 50% blood serum, with an interference response of less than 3% of the assay response in pure buffer solution. FIG. 5 shows the "ex situ" assay calibration curve of insulin detection in 50% blood serum. A similar linear range to that of the assays in pure buffer solution was obtained, with a detection limit of 4.77±0.99 pM.

Results—Biosensor Regeneration

Biosensor regeneration was achieved by surface immersion in 0.2 M Gly-HCl buffer containing 1% DMSO for 5 min to disassociate the insulin antibody-antigen complex. Subsequent to this, the electrodes can be re-used in assays with minimal detriment to sensitivity (<4% deviation in sensitivity across 4 repeated generations assessments and regenerations—see FIG. 6).

EXAMPLE 2

Insulin Detection by Non-Faradaic EIS, Via Phase Analysis, on a Betaine Polymer-modified Electrode Chemicals and Reagents Human insulin, human blood serum, strepavidin and bovine serum albumin (BSA) were purchased from Sigma Aldrich. Monoclonal anti-insulin antibody (mouse IgG1 isotype) was purchased from Santa Cruz Biotechnology, Inc. 1-ethyl-3-(3-dimethylaminopropyl) carbodiimide (EDC) and N-hydroxysuccinimde (NETS) were purchased from Sigma Aldrich. β-Propiolactone was purchased from Alfa Aesar. 2-(Dimethylamino)ethyl methacrylate (DMAEM), anhydrous acetone, Ethylene glycol dimethacrylate (EGDMA) and the photoinitiator 2-Hydroxy-2-methylpropiophenone were purchased from Sigma Aldrich.

Phosphate buffered saline (PBS, 10 mM, pH 7.4) was prepared by dissolving PBS tablets (Sigma Aldrich) in ultrapure water, and filtered using a 0.22 μm membrane filter. All other chemicals were of analytical grade. Ultrapure water (18.2 MΩ/cm) was obtained from a Milli-Q system and used throughout.

Apparatus

Electrochemical experiments were performed on an Autolab Potentiostat 12 equipped with an FRA2 module (Metrohm Autolab B.V.). A conventional three-electrode system with gold disk working electrodes (1.6 mm diameter, BASi), a platinum wire counter, and a silver/silver chloride (Ag/AgCl, filled with 1.0 M KCl) reference electrode (CH Instruments) was used. All potentials reported are relative to the Ag/AgCl reference electrode. The ultraviolent (UV) polymerisation was carried out with a UV lamp (CAMAG).

Sensor Surface Preparation

The monomer carboxybetaine methacrylate (CBMA) was synthesized according to known methods. Briefly, 10 mL of 12 mM β-Propiolactone in acetone was added dropwise to a 50 mL 10 mM DMAEM in anhydrous acetone, and the reaction mixture was stirred under nitrogen protection at 15° C. for 5 h. The white precipitate was washed with 50 mL of anhydrous acetone and 100 mL of anhydrous ether. The product was dried under reduced pressure to obtain the final CBMA monomer product, and the monomer was kept at 2-8° C. before polymerisation.

Gold electrodes were first polished sequentially with 3.0, 1.0 and 0.1 μm diamond spray then ultrasonically washed in water (ca. 5 min) prior to immersion in freshly prepared piranha solution (concentrated $H_2SO_4$: 30% $H_2O_2$, v/v 3:1. Caution: please treat with extreme care!) for 15 min. Finally, the electrodes were electrochemically pre-treated b, cyclic voltammetry (CV) scans in 0.5 M KOH over the potential range from −0.35 V to −1.35 V at a scan rate of 2 V/s, until curves were stable. Following this treatment, scans were carried out in 0.5 M $H_2SO_4$ over the potential range from −0.35 to 1.5 V (4 V/s) until a stable sharp reduction peak is obtained.

The pre-treated gold electrodes were dried in a flow of nitrogen gas and immediately immersed in a solution of 5 mM cysteamine in ethanol for 12 hours at room temperature. After monolayer formation electrodes were rinsed with ethanol, then water and dried in a flow of nitrogen gas, prior to incubation in a solution containing 0.4 M EDC, 0.1 M NHS and 0.5 mM CBMA to attach the CBMA to the terminal amine groups (3 hours). Following the attachment of CBMA, 1.0 μL of photopolymerisation solution (prepared by dissolving 17.2 mg CBMA, 0.2 mg EGDMA and 1.17 mg photoinitiator in 0.1 mL water) was drop-coated onto the Au electrode surface, and the photopolymerisation reaction was carried out at 25° C. for 30 min under 254 nm UV light to form poly(carboxybetaine) methacrylate (PCBMA). The PCBMA modified electrode was then soaked in 10 mM PBS (change the PBS after 30 min) for 12 h to release the un-reacted chemicals and equilibrate the hydrogel-like polymer.

In order to attach the insulin antibody to the PCBMA modified electrode, the electrode was firstly immersed in a solution containing 0.4 M EDC and 0.1 M NHS for 30 min to activate the terminal carboxyl groups, and after washing with PBS, insulin antibodies were immobilized by dipping the electrode in a 1.0 μM antibody solution (10 mM PBS, pH 7.4) for 3 hours at room temperature. In order to deactivate the un-reacted terminal groups, the modified electrode was finally soaked in 100 μM BSA for 1 hour at room temperature, then rinsed with PBS and stored in PBS prior to analysis.

Electrochemical Impedance Spectroscopy

Non-Faradaic electrochemical impedance spectroscopy (EIS) measurements were conducted with an Autolab Potentiostat 12 equipped with an FRA2 module using a three-electrode system and a frequency range of 0.1 Hz to 100 kHz, or 100 Hz if stated, with the potential set at 0 V. All analyses were carried out in 10 mM pH 7.4 PBS, and plotted in the form of Bode plots, and the recorded phase at 0.2 Hz was used for analysis.

Sensor Operation

For the detection of insulin, the prepared receptive interfaces were incubated in 10 mM pH 7.4 PBS containing specific concentrations of insulin at room temperature for 30 min, and EIS responses were recorded in pure PBS after through rinsing with PBS. FIG. 7 shows that the phase change data extracted from the non-Faradaic EIS measurements is capable of determining concentration of insulin down to sub-pM levels.

To evaluate sensor selectivity, BSA and PBS containing different volume of human serum (1%, 5%, 10%, 20%, 50%, 80% and 100%) were tested similarly. FIG. 8 shows that there is substantially no interference/fouling effect on the phase change EIS signal arising in the non-insulin-containing samples.

The error bars in the reported data represent the standard deviation of three measurements.

Summary

The assay system of Example 2, which is based on non-Faradaic EIS, analysed via phase change data, and which utilises the polymer-modified electrode surface described herein, shows enhanced performance (e.g., better linear fit, better limit of detection and demonstration with 100% serum carrier media) compared with the assay system of Example 1.

EXAMPLE 3

Further Data Relating to Insulin Detection by Non-Faradaic EIS, Via Phase Analysis, on a Betaine Polymer-modified Electrode Some further properties of the electrodes and methods of the invention were investigated. The electrodes were manufactured, and EIS performed, substantially as described in Example 2.

The stability of the chemisorbed zwitterionic PCBMA polymer interface (prior to coupling of the anti-insulin antibodies) was assessed by EIS. The interface found to show excellent stability over one month. In particular, as shown in FIG. 10, non-Faradaic Bode phase plots of the electrode were recorded at different time intervals across 32 days in PBS (10 nM, pH 7.4). The standard deviation of the recorded phase at 0.2 Hz was found to be less than 0.5%, indicating excellent interfacial stability. Note that hydrogel and extreme hydrophilic nature of these films preclude any meaningful SEM, TEM, spectroscopic, contact angle or ellipsometric characterisation.

FIG. 11 shows both the impedance change and the phase obtained by carrying out the present non-Faradaic EIS technique in 10 mM PBS (pH 7.4), at a frequency range of 0.1-100 KHz, on samples containing different amounts of insulin (0 pM, 1 pM, 10 pM, 100 pM and 2000 pM). The latter, which is independent of electrode surface area, was monitored by standard impedance methods. It can already be seen from this Figure that sensitivity to changes in insulin concentration is much greater when assessing phase change rather than impedance, particularly in the low frequency region. FIG. 12 further compares (A) phase change curves against (B) impedance curves at selected frequencies. FIG. 13 shows in more detail still the neat phase changes recorded in the low frequency domain and demonstrates how the sampling frequency can readily be optimised to the most sensitive response to insulin (here 0.2 Hz, corresponding to a log {frequency} value of around −0.7 on the x-axis of the Figure). Note that the fluctuation in the middle of the curves is merely a potentiostat artefact and has no impact on the validity of the measurements.

To confirm the applicability of the method to quantitative sensing in neat blood serum, assays of insulin spiked into different serum solutions were carried out and revealed quantification to consistently be within 2% of that in pure PBS (see FIG. 14).

The application of the interfaces to the quantification of insulin in a cohort of patient samples (spanning a broad range of concentrations) is summarized in FIG. 15, where it is evident that the assays are well behaved and compare well (most results being within 5% of each other) with comparative quantification of the same samples by a standard chemiluminescence assay. A more detailed Bland Altman analysis across patient samples assessed at both macro gold electrodes and microelectrode arrays is shown in FIG. 16, where the quantification differences between EIS and chemiluminescence are largely within 10% across the entire concentration range. This is highly encouraging as current levels of agreement between commonly used methods in clinical use can show up to 200% variation in results through differences in assay sensitivity and specificity.

The work leading to this invention has received funding from the European Union Seventh Framework Agreement (FP7/2007-2013) under grant agreement no. 271775.

The invention claimed is:

1. A multi-step method of making an electrode for use in an electrochemical impedance spectroscopy technique, the method comprising:
   (a) contacting a surface of a substrate with a first composition comprising photopolymerisable monomers to covalently attach the photopolymerisable monomers to the surface of the substrate, thereby obtaining a modified surface having a layer of photopolymerisable monomers covalently attached thereto; and then, after covalent attachment of said layer of photopolymerisable monomers is complete,
   (b) contacting said modified surface with a second composition different from the first composition, and comprising further photopolymerisable monomers and optionally crosslinking monomers, and photochemically polymerising the photopolymerisable monomers, thereby generating an electrode comprising polymers disposed on said surface;
   wherein the photopolymerisable monomers of step (a) are the same as the further photopolymerisable monomers of step (b).

2. A method according to claim 1, wherein the photopolymerisable monomers each comprise a photopolymerisable carbon-carbon double bond.

3. A method according to claim 1, wherein the photopolymerisable monomers are photopolymerisable betaine monomers.

4. A method according to claim 3, wherein the photopolymerisable betaine monomers each comprise a quaternary ammonium cation and a carboxylate group.

5. A method according to claim 4, wherein the photopolymerisable betaine monomers have the formula (II)

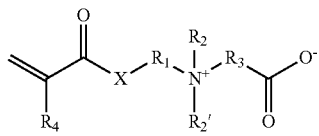

(II)

wherein:
$R_1$ and $R_3$ are the same or different and are each a $C_1$ to $C_5$ alkylene group;
$R_2$ and $R_{2'}$ are the same or different and are each a $C_1$ to $C_5$ alkyl group;
$R_4$ is a hydrogen atom or a $C_1$ to $C_5$ alkyl group; and
X is O or NH.

6. A method according to claim 5, wherein the photopolymerisable betaine monomers are selected from carboxybetaine methacrylate (CBMA), carboxybetaine acrylamine (CBAA) and carboxybetaine ethylacrylate (CBEA).

7. A method according to claim 1, which further comprises (c) attaching probe molecules capable of specific binding to a target species to said polymers.

8. A method according to claim 7, wherein the target species is insulin.

9. A method according to claim 1, wherein the layer of polymerisable monomers covalently attached to the surface of the substrate in step (a) is a layer of photopolymerisable monomers attached to the surface of a gold substrate via gold-sulfur bonds.

10. A multi-step method of making an electrode for use in an electrochemical impedance spectroscopy technique, the method comprising:
 (a) contacting a surface of a substrate with a first composition to covalently attach the first composition to the surface of the substrate, thereby obtaining a modified surface having a layer of the first composition covalently attached thereto;
 (b) contacting said modified surface with a second composition, different from the first composition, and comprising photopolymerisable monomers to covalently attach the photopolymerisable monomers to the modified surface, thereby obtaining a further modified surface;
 (c) contacting the further modified surface with a third composition comprising additional photopolymerisable monomers and optionally crosslinking monomers, wherein the third composition is different from the second composition; and
 (d) photochemically polymerising the photopolymerisable monomers, thereby generating an electrode comprising polymers disposed on said surface;
wherein the photopolymerisable monomers of step (b) are the same as the additional photopolymerisable monomers of step (c).

11. A method according to claim 10, wherein the photopolymerisable monomers each comprise a photopolymerisable carbon-carbon double bond.

12. A method according to claim 10, wherein the photopolymerisable monomers are photopolymerisable betaine monomers.

13. A method according to claim 12, wherein the photopolymerisable betaine monomers each comprise a quaternary ammonium cation and a carboxylate group.

14. A method according to claim 13, wherein the photopolymerisable betaine monomers have the formula (II)

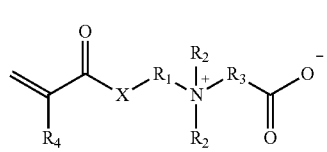

(II)

wherein:
$R_1$ and $R_3$ are the same or different and are each a $C_1$ to $C_5$ alkylene group;
$R_2$ and $R_{2'}$ are the same or different and are each a $C_1$ to $C_5$ alkyl group;
$R_4$ is a hydrogen atom or a $C_1$ to $C_5$ alkyl group; and
X is O or NH.

15. A method according to claim 14, wherein the photopolymerisable betaine monomers are selected from carboxybetaine methacrylate (CBMA), carboxybetaine acrylamine (CBAA) and carboxybetaine ethylacrylate (CBEA).

16. A method according to claim 10, further comprising (e) attaching probe molecules capable of specific binding to a target species to the polymers.

17. A method according to claim 16, wherein the target species is insulin.

18. A method according to claim 10, wherein the first composition covalently attached to the surface of the substrate in step (a) is attached to a gold substrate surface via gold-sulfur bonds.

* * * * *